(12) United States Patent
Babcock et al.

(10) Patent No.: US 9,023,393 B2
(45) Date of Patent: May 5, 2015

(54) PHARMACEUTICAL COMPOSITIONS OF ADSORBATES OF AMORPHOUS DRUGS AND LIPOPHILIC MICROPHASE-FORMING MATERIALS

(75) Inventors: Walter C. Babcock, Bend, OR (US);
Dwayne T. Friesen, Bend, OR (US);
Ravi M. Shanker, Groton, CT (US);
Daniel T. Smithey, Bend, OR (US)

(73) Assignee: Bend Research, Inc., Bend, OR (US)

( * ) Notice: Subject to any disclaimer, the term of this patent is extended or adjusted under 35 U.S.C. 154(b) by 1975 days.

(21) Appl. No.: 10/910,448

(22) Filed: Aug. 3, 2004

(65) Prior Publication Data

US 2005/0031693 A1 Feb. 10, 2005

Related U.S. Application Data

(60) Provisional application No. 60/492,410, filed on Aug. 4, 2003.

(51) Int. Cl.
*A61K 9/14* (2006.01)
*A61K 9/16* (2006.01)
*A61K 47/44* (2006.01)
*A61K 47/12* (2006.01)
*A61K 47/26* (2006.01)

(52) U.S. Cl.
CPC .............. *A61K 9/143* (2013.01); *A61K 9/1611* (2013.01); *A61K 47/12* (2013.01); *A61K 47/26* (2013.01); *A61K 47/44* (2013.01)

(58) Field of Classification Search
CPC ..... A61K 9/143; A61K 9/1611; A61K 47/44; A61K 47/26; A61K 47/12
USPC ......................................................... 424/486
See application file for complete search history.

(56) References Cited

U.S. PATENT DOCUMENTS

| | | | | |
|---|---|---|---|---|
| 4,343,789 A | 8/1982 | Kawata et al. | | 424/78 |
| 4,581,232 A | 4/1986 | Peters et al. | | 424/155 |
| 4,711,774 A | 12/1987 | Denick, Jr. et al. | | 424/48 |
| 4,716,033 A | 12/1987 | Denick, Jr. | | 424/48 |
| 4,717,565 A | 1/1988 | Denick, Jr. | | 424/155 |
| 4,719,228 A | 1/1988 | Rawlins | | |
| 4,772,627 A | 9/1988 | Matsui et al. | | 514/462 |
| 4,835,186 A | 5/1989 | Reuter et al. | | 514/570 |
| 4,973,469 A | 11/1990 | Mulligan et al. | | 424/461 |
| 5,008,114 A | 4/1991 | Lovrecich | | 424/484 |
| 5,015,479 A | 5/1991 | Mulligan et al. | | 424/457 |
| 5,128,142 A * | 7/1992 | Mulligan et al. | | 424/457 |
| 5,281,420 A | 1/1994 | Kelm et al. | | 424/452 |
| 5,449,521 A | 9/1995 | Lovrecich | | 424/489 |
| 5,505,959 A | 4/1996 | Tachon et al. | | 424/450 |
| 5,580,546 A | 12/1996 | Ser et al. | | 424/59 |
| 5,610,193 A | 3/1997 | Al-Razzak et al. | | 514/616 |
| 5,626,878 A * | 5/1997 | Garay et al. | | 424/489 |
| 5,700,485 A | 12/1997 | Berde et al. | | 424/501 |
| 5,723,269 A | 3/1998 | Akagi et al. | | 424/497 |
| 5,759,997 A | 6/1998 | Cavanak | | |
| 5,773,021 A * | 6/1998 | Gurtler et al. | | 424/427 |
| 5,925,645 A | 7/1999 | Schmidt et al. | | 514/277 |
| 5,932,587 A | 8/1999 | Schmeck et al. | | 514/278 |
| 5,993,858 A | 11/1999 | Crison et al. | | 424/490 |
| 6,004,973 A | 12/1999 | Guitard et al. | | 514/291 |
| 6,015,797 A * | 1/2000 | Camborde et al. | | 514/46 |
| 6,063,788 A | 5/2000 | Brandes et al. | | 514/290 |
| 6,069,148 A | 5/2000 | Schmidt et al. | | 514/277 |
| 6,107,290 A | 8/2000 | Woo et al. | | |
| 6,121,330 A | 9/2000 | Muller-Gliemann et al. | 514/730 |
| 6,127,383 A | 10/2000 | Schmidt et al. | | 514/312 |
| 6,140,342 A | 10/2000 | Goldstein et al. | | 514/313 |
| 6,140,343 A | 10/2000 | DeNinno et al. | | 514/313 |
| 6,147,089 A | 11/2000 | DeNinno et al. | | 514/313 |
| 6,147,090 A | 11/2000 | DeNinno et al. | | 514/313 |
| 6,191,162 B1 | 2/2001 | Byrd et al. | | |
| 6,197,781 B1 | 3/2001 | Guitard et al. | | 514/291 |
| 6,197,786 B1 | 3/2001 | DeNinno et al. | | 514/313 |
| 6,207,671 B1 | 3/2001 | Schmidt et al. | | 514/277 |
| 6,254,889 B1 | 7/2001 | Kigoshi et al. | | 424/487 |
| 6,264,981 B1 | 7/2001 | Zhang et al. | | 424/451 |
| 6,280,770 B1 | 8/2001 | Pather et al. | | 424/465 |
| 6,291,477 B1 | 9/2001 | Schmidt et al. | | 514/311 |
| 6,294,192 B1 * | 9/2001 | Patel et al. | | 424/451 |
| 6,310,075 B1 | 10/2001 | DeNinno et al. | | 514/313 |
| 6,312,704 B1 | 11/2001 | Farah et al. | | 424/401 |
| 6,316,497 B1 | 11/2001 | Liu et al. | | 514/475 |
| 6,362,198 B1 | 3/2002 | Goldstein et al. | | 514/313 |
| 6,426,365 B1 | 7/2002 | Shinkai et al. | | 514/513 |

(Continued)

FOREIGN PATENT DOCUMENTS

| | | | | |
|---|---|---|---|---|
| EP | 0429187 | 1/1994 | | A61K 9/18 |
| EP | 0440702 | 4/1994 | | A61K 9/18 |

(Continued)

OTHER PUBLICATIONS

Takeuchi, Chem. Pharm. Bull. 35(9), 1987, pp. 3800-3806.
Monkhouse et al., J. Pharm. Sci, vol. 61, No. 9, 1972.
Patent Abstracts of Japan vol. 2000, No. 4, Aug. 31, 2000 & JP 2000 016934 A, Jan. 18, 2000.
Chowdary et al., "Enhancement of Dissolution Rate of Meloxicam," Indian Journal of Pharmaceutical Sciences, Apr.-Mar. 2001, 150-154.

(Continued)

*Primary Examiner* — Blessing M Fubara
(74) *Attorney, Agent, or Firm* — Klarquist Sparkman, LLP

(57) ABSTRACT

A pharmaceutical composition comprises a solid adsorbate comprising a drug adsorbed onto a substrate and a lipophilic microphase-forming material. The solid adsorbate may also be co-administered with a lipophilic microphase-forming material to an in vivo use environment. The compositions of the present invention enhance the concentration of drug in a use environment.

16 Claims, No Drawings

(56) References Cited

U.S. PATENT DOCUMENTS

| | | | |
|---|---|---|---|
| 6,436,441 B1 | 8/2002 | Sako et al. | |
| 6,548,555 B1 | 4/2003 | Curatolo et al. | |
| 6,602,523 B1 | 8/2003 | Joshi | 424/489 |
| 2001/0009677 A1 | 7/2001 | Bruce et al. | 424/464 |
| 2001/0044409 A1 | 11/2001 | Ghebre-Sellassie et al. | 514/26 |
| 2001/0053791 A1 | 12/2001 | Babcock et al. | |
| 2002/0103225 A1* | 8/2002 | Curatolo et al. | 514/313 |
| 2003/0022944 A1* | 1/2003 | Gumkowski et al. | 514/786 |
| 2003/0054037 A1* | 3/2003 | Babcock et al. | 424/486 |
| 2003/0099708 A1* | 5/2003 | Rowe et al. | 424/469 |
| 2003/0129239 A1 | 7/2003 | Goldstein | 424/486 |

FOREIGN PATENT DOCUMENTS

| | | | |
|---|---|---|---|
| EP | 0852140 | 7/1998 | A61K 9/00 |
| EP | 0901786 | 3/1999 | A61K 9/14 |
| EP | 0943327 | 9/1999 | |
| EP | 1027885 | 8/2000 | A61K 9/14 |
| EP | 1027886 | 8/2000 | A61K 9/14 |
| EP | 1027887 | 8/2000 | A61K 9/26 |
| EP | 1027888 | 8/2000 | A61K 9/26 |
| JP | 7291854 | 11/1996 | |
| JP | 2000-16934 A | 1/2000 | |
| SI | 9500059 | 8/1996 | |
| WO | WO9001329 | 2/1990 | |
| WO | WO 9004962 | 3/1990 | A61K 9/18 |
| WO | WO9619239 | 6/1996 | |
| WO | WO 9800528 | 2/1998 | C07D 213/20 |
| WO | WO 9831360 | 7/1998 | A61K 31/19 |
| WO | WO 9831361 | 7/1998 | A61K 31/215 |
| WO | WO 9834920 | 8/1998 | C07D 312/74 |
| WO | WO 9835937 | 8/1998 | C07C 323/40 |
| WO | WO 9838167 | 9/1998 | C07D 215/54 |
| WO | WO 9839299 | 9/1998 | C07D 215/20 |
| WO | WO9906044 | 2/1999 | |
| WO | WO 9908660 | 2/1999 | A61K 9/14 |
| WO | WO 9914174 | 3/1999 | C07C 35/52 |
| WO | WO 9914204 | 3/1999 | C07D 249/12 |
| WO | WO 9914215 | 3/1999 | C07D 215/20 |
| WO | WO 9915487 | 4/1999 | C07C 33/50 |
| WO | WO9927946 | 6/1999 | |
| WO | WO 9940061 | 8/1999 | C07C 231/00 |
| WO | WO 9941237 | 8/1999 | C07D 213/80 |
| WO | WO 0000179 | 1/2000 | A61K 9/14 |
| WO | WO 0018721 | 4/2000 | C07C 215/16 |
| WO | WO 0018723 | 4/2000 | C07C 217/52 |
| WO | WO 0018724 | 4/2000 | C07C 217/90 |
| WO | WO 00/38722 * | 7/2000 | |
| WO | WO 0057881 | 10/2000 | A61K 31/47 |
| WO | WO 0100180 | 1/2001 | A61K 9/48 |
| WO | 01/10410 A1 | 2/2001 | |
| WO | WO 0110410 | 2/2001 | A61K 9/10 |
| WO | WO 0115664 | 3/2001 | A61K 9/00 |
| WO | WO 0130288 | 5/2001 | A61F 13/02 |
| WO | WO0140190 | 6/2001 | |
| WO | WO0141765 | 6/2001 | |
| WO | WO0142221 | 6/2001 | |
| WO | 01/47495 A1 | 7/2001 | |
| WO | WO 0147495 | 7/2001 | A61K 9/14 |
| WO | WO0147498 | 7/2001 | |
| WO | WO0147500 | 7/2001 | |
| WO | WO 0154667 | 8/2001 | A61K 9/14 |
| WO | 01/68055 A1 | 9/2001 | |
| WO | WO 0168055 | 9/2001 | A61K 9/14 |
| WO | WO 0195939 | 12/2001 | A61K 47/32 |
| WO | WO 0211710 | 2/2002 | A61K 31/00 |
| WO | 03/000238 A1 | 1/2003 | |
| WO | WO 03000238 | 1/2003 | A61K 9/18 |
| WO | WO03004060 | 1/2003 | |
| WO | 03/063833 A1 | 8/2003 | |
| WO | WO 03063833 | 8/2003 | A61K 9/16 |

OTHER PUBLICATIONS

Data Sheet for European Application No. 03-700-435.5 (Oct. 2006).
Kerc et al., "Alternative solvent-free preparation methods for felodipine surface solid dispersions," Drug Development and Industrial Pharmacy, 24(4), 359-363 (Apr. 1998).
Kerc et al., "Dissolution study of felodipine solid dispersions," Acta Pharm. 43, 113-120 (1993).
Kerc et al., "Use of hydrophilic carriers in enhancement of felodipine dissolution," Acta Pharm. Jugosl. 41, 259-265 (1991).
Konno et al. "Physical and chemical changes of medicinals in mixtures with adsorbents in the solid state. I. Effect of vapor pressure of the medicinals on changes in crystalline properties," Chem. Pharm. Bul. 34 (1) 301-307 (Jan. 1986).
F. Lallemand et al., "A water-soluble prodrug of Cyclosporine a for Ocular Application: A Stability Study," European Journal of Pharmaceutical Sciences, Sep. 26, 2005 124-129.
JP-11246404 Patent Abstracts of Japan.
D.C. Monkhouse et al., Journal of Pharmaceutical Sciences, 61:9, pp. 1435-1141, 1972.
A.Y. Gore et al., Journal of Pharmaceutical Sciences, 68:2, pp. 197-202, 1979.
H. Takenaka et al., Journal of Pharmaceuticals Sciences, 69:12, pp. 1388-1392, 1980.
R. Daniels et al., Drug Development and industrial Pharmacy, 12:11, pp. 2127-2156, 1986.
H. Takeuchi et al., Chem. Pharm. Bull, 35:9, pp. 3800-3806, 1987.
A.H. Abd El-Gawad et al., Pharmazie, 43, pp. 624-627, 1988.
K. Takada et al., Chem. Pharm. Bull, 37:9, pp. 2542-2544, 1989.
K. Takada et al., Chem. Pharm. Bull, 37:2, pp. 471-474, 1989.
T. Konno, Chem. Pharm. Bull, 38:4, pp. 1032-1034, 1990.
S.A. Charman et al., Pharmaceutical Research, 9:1, pp. 87-93, 1992.
E.S. Saers et al., International Journal of Pharmaceutics, 90, pp. 105-118, 1993.
P.C. Sheen et al., International Journal of Pharmaceutics, 118, pp. 221-227, 1995.
T. Oguchi et al., Yakazaigaku, 57:3, pp. 168-173, 1997.
S. M. Alsaidan et al., Drug Development and Industrial Pharmacy, 14:4, pp. 389-394, 1998.
I. Katzhendler et al., Journal of Controlled Release, 54, pp. 69-85, 1998.
T. Gershanik et al., European Journal of Pharmaceutics and Biopharmaceutics, 50, pp. 179-188, 2000.
K. Yamamoto et al., Adsorption of Pharmaceutical Organic Compounds, chp. 29, pp. 763-779, 1999.

* cited by examiner

PHARMACEUTICAL COMPOSITIONS OF ADSORBATES OF AMORPHOUS DRUGS AND LIPOPHILIC MICROPHASE-FORMING MATERIALS

This application is filed claiming priority from U.S. Provisional Application No. 60/492,410 filed Aug. 4, 2003.

FIELD OF THE INVENTION

The present invention relates to pharmaceutical compositions comprising (1) a solid adsorbate comprising a low-solubility drug adsorbed onto a substrate, and (2) a lipophilic microphase-forming material that enhances the concentration of the drug in a use environment.

BACKGROUND OF THE INVENTION

Low-solubility drugs often show poor bioavailability or irregular absorption, the degree of irregularity being affected by factors such as dose level, fed state of the patient, and form of the drug. Increasing the bioavailability of low-solubility drugs has been the subject of much research. Increasing bioavailability depends on improving the concentration of dissolved drug in solution to improve absorption.

It is well known that the amorphous form of a low-solubility drug that is capable of existing in either the crystalline or amorphous form may temporarily provide a greater aqueous concentration of drug relative to the equilibrium concentration obtained by dissolution of the drug in a use environment. Such amorphous forms may consist of the amorphous drug alone, a dispersion of the drug in a matrix material, or the drug adsorbed onto a substrate. It is believed that such amorphous forms of the drug may dissolve more rapidly than the crystalline form, often dissolving faster than the drug can precipitate from solution. As a result, the amorphous form may temporarily provide a greater-than equilibrium concentration of drug.

While such amorphous forms may show initially enhanced concentration of the drug in a use environment, nevertheless the improved concentration is often short-lived. Typically, the initially enhanced drug concentration is only temporary and quickly returns to the lower equilibrium concentration.

One problem with using the amorphous form of a drug is that the solid drug may not be stable physically in the amorphous form. Often the crystalline form of the drug has a lower free energy, and thus over time, the amorphous drug will tend to crystallize. The rate of crystallization may be influenced by storage conditions, such as temperature and humidity, as well as the constituents of the composition.

Babcock, et al. in commonly assigned U.S. patent application Ser. No. 10/173,987 published as US 2003/0054037, incorporated herein by reference, disclose a solid adsorbate comprising a low-solubility drug adsorbed onto a substrate, the substrate having a surface area of at least 20 m$^2$/g, wherein at least a major portion of the drug in the adsorbate is amorphous. The composition provides enhanced drug concentrations when administered to an aqueous environment of use. In another embodiment, the composition comprises a solid adsorbate of a low-solubility drug adsorbed onto a substrate mixed with a concentration-enhancing polymer. In yet another embodiment, the composition comprises a solid adsorbate and a concentration-enhancing polymer adsorbed onto a substrate.

Babcock, et al. disclose that the adsorbate may be mixed with surfactants or surface-active agents to increase the rate of dissolution by facilitating wetting, formation of micelles, or inhibiting crystallization or precipitation of the drug. Such materials can comprise up to 5 wt % of the composition.

Takeuchi, Chem. Pharm. Bull. 35(9) 3800-3806 (1987), discloses spray dried compositions of the drug tolbutamide and very fine hydrophilic silica particles, Aerosil® 200. A 1:1 weight solution of tolbutamide and Aerosil® 200 was sprayed from a solution of 2% ammonia water. The authors indicate that at least some of the drug was amorphous.

Reuter et al., U.S. Pat. No. 4,835,186 discloses a spray dried suspension of colloidal silica in a lower alkanol solution of ibuprofen and cellulose acetate phthalate. The examples disclose spray dried compositions comprising ibuprofen, CAP, colloidal silica and a small amount of castor oil, spray dried from a solution of ethyl acetate and isopropyl alcohol.

WO 01/00180A1 discloses a self-emulsifying drug (SED) composition comprising a o-(chloroacetylcarbamoyl)fumigillol, a pharmaceutically acceptable carrier comprising an oily constituent and at least one surfactant, and a stabilizing component, the stabilizing component comprising water, an acid, and an adsorbent core complex forming agent. The pharmaceutically acceptable carrier having the drug can be filled, mixed, adsorbed, filtered, or otherwise combined with the adsorbent or complex forming agent. Exemplary adsorbents include active charcoal and silica gel.

Monkhouse et al. (*J. Pharm. Sci.*, Vol. 61, No. 9, 1972), disclose forming adsorbents by mixing a drug and water insoluble adsorbent such as fumed silicon dioxide or precipitated silicic acid, adding a sufficient quantity of an organic solvent to dissolve the drug, and then evaporating the solvent by a stream of filtered air.

Yamamoto et al., "Adsorption of Pharmaceutical Organic Compounds onto Porous Materials," (in *Surfaces of Nanoparticles and Porous Materals*, Scwarz and Contescu eds, 1999) reviews among other things, improving dissolution of drugs by using porous materials to form drug that is the amorphous state.

Nevertheless, what is still desired is a composition that may enhance the dissolution and/or bioavailability of poorly soluble drugs. These needs and others that will become apparent to one of ordinary skill are met by the present invention, which is summarized and described in detail below.

BRIEF SUMMARY OF THE INVENTION

The present invention overcomes the drawbacks of the prior art by providing a composition comprising (1) a solid adsorbate comprising a low-solubility drug adsorbed onto a substrate, wherein at least a major portion of the drug is amorphous, and (2) a lipophilic microphase-forming material. The combination of a solid adsorbate and a lipophilic microphase-forming material results in improved dissolved concentration of the drug in the aqueous use environment, and in some embodiments a surprising synergy. A concentration-enhancing polymer may optionally be incorporated into the solid adsorbate or mixed with the composition of the present invention.

In another aspect of the invention, a solid adsorbate comprising a low-solubility drug adsorbed onto a substrate, wherein at least a major portion of the drug is amorphous, is co-administered with a lipophilic microphase-forming material to an in vivo use environment. The solid adsorbate may optionally include a concentration-enhancing polymer, or a concentration-enhancing polymer may optionally be co-administered with the solid adsorbate and lipophilic microphase-forming material. Another aspect of the invention comprises a kit comprising a solid adsorbate comprising a low-solubility drug adsorbed onto a substrate and a lipophilic microphase-forming material.

The present inventors have found that the ability of a drug/substrate adsorbate to enhance the concentration of drug in a use environment may be significantly improved by the addition of certain lipophilic microphase-forming materials. These lipophilic microphase-forming materials, when administered to an aqueous use environment such as the GI tract, form a plurality of small microphases, or so-called "lipophilic microphases." The lipophilic microphase-forming materials are chosen such that (1) they are water immiscible, (2) the drug has a high partition coefficient between the lipophilic microphase-forming material and the aqueous use environment, and (3) they form small lipophilic microphases in the aqueous use environment.

Without wishing to be bound by any particular theory, the present inventors believe that when a composition of the present invention comprising an adsorbate comprising a low-solubility drug and a high-surface-area substrate, wherein at least a major portion of the drug is amorphous, and a lipophilic microphase-forming material are introduced to a use environment such as the GI tract, the drug may be present in several different species. When the aqueous use environment is either the GI tract of an animal, or an in vitro use environment that simulates the GI tract of an animal, it is believed that at least five different drug species are formed: (1) free drug; (2) drug present within bile salt micelles that are naturally occurring in the GI tract; (3) drug adsorbed to small particles of the high-surface-area substrate; (4) precipitate; and (5) drug in lipophilic microphases.

As used herein, the term "free drug" refers to drug molecules which are dissolved in the aqueous solution and are generally either monomeric or clusters of no more than about 100 molecules. "Precipitate" is a general term for any relatively large particulates that form and fall out of solution, either naturally or upon centrifugation. Such precipitate may comprise one or more or all of the following forms: (1) crystalline drug; (2) amorphous drug; and/or (3) drug adsorbed to the substrate that is present as particles that have a sufficient density and size so as to drop out of solution (typically greater than about 5 to 10 microns in average diameter). As used herein, the term "total dissolved drug" refers to the total concentration of drug in a use environment that is not present as precipitate. Thus, "total dissolved drug" refers to the sum of all drug species that are present except for precipitate. These species include, but are not limited to, free drug, drug within bile salt micelles, drug adsorbed to small particles, and drug in the lipophilic microphases.

Generally, it is desirable to increase the free drug concentration in the GI tract. Without wishing to be bound by any particular theory or mechanism of action, it is believed that primarily free drug is directly absorbed from the GI tract into the blood. The absorption rate of a drug from the GI tract to the blood is therefore generally proportional to the free drug concentration at the intestinal membrane surface. Drug present in the other species generally must first convert to the free drug form in order to be absorbed. In addition, for many lipophilic drugs, the rate limiting step for absorption can be diffusion across the mucin or mucus layer that coats the lipid membrane of the intestinal Wall. This layer is often referred to as the "unstirred water layer." When diffusion across this layer is rate limiting, the absorption rate of drug is proportional to the sum of the free drug and drug in species such as bile-salt micelles or lipophilic microphases, which can diffuse across the unstirred water layer, normalized for their respective diffusion coefficients.

The present invention provides one or more of the following advantages over prior methods for enhancing the concentration and bioavailability of low-solubility drugs. The lipophilic microphases are capable of sufficiently solubilizing the drug in the use environment to enhance bioavailability. In some cases, the lipophilic microphases are thought to be (1) highly mobile, meaning that they may diffuse more rapidly than precipitate throughout the use environment and particularly through the unstirred water layer of the intestinal wall; and (2) labile, meaning that the drug may rapidly convert back and forth between the lipophilic microphases and free drug. Because the lipophilic microphases solubilize the drug, the lipophilic microphases may reduce the formation of drug precipitate and increase the amount of total dissolved drug. The lability of the lipophilic microphases may also increase the rate of resupply of free drug in the use environment. As free drug is absorbed, drug present in the lipophilic microphases may rapidly convert to free drug, thus maintaining a sustained free drug concentration. When the lipophilic microphases are small, their high mobility may also increase the rate of drug absorption through the intestinal wall by increasing the transport rate of the drug through the unstirred water layer of the intestinal wall. In combination, these properties may greatly enhance the rate and extent of drug absorption (e.g., bioavailability).

In addition, the compositions may also have the advantage of providing more similar absorption levels between the fed and fasted state of a set of patients, as well as less variation in the level of absorption from patient to patient. A problem when dosing low-solubility drugs is that the absorption of the drug may vary widely between the fed and fasted state of the patient. This variation in absorption is due in part to variation in the level of bile-salt micelles between the fasted and fed states. The lipophilic microphase-forming materials of the present invention can function in a similar manner as bile-salt micelles.

As mentioned above, it is well known in the art that in the fed state, the concentration of bile-salt micelles present in the GI tract is greater than the concentration present in the fasted state. The inventors believe that this difference in the concentration of bile-salt micelles in the GI tract in the fed versus fasted state may account, at least in part, for the fed/fasted differences in bioavailability observed for many pharmaceutical compositions. The compositions of the present invention comprising a drug/substrate adsorbate and a lipophilic microphase-forming material may minimize this fed/fasted difference in bioavailability. The compositions tend to equalize the amount of drug present in highly labile, highly mobile species between the fed and fasted state, and thus provide a more uniform bioavailability between the fed and fasted state. This equalization can be understood via a hypothetical example in which lipophilic drug with an aqueous solubility of 1 µgA/mL and a bile salt aqueous partition coefficient of 200, is dosed in the fed and fasted states with and without lipophilic microphase-forming material ("µgA" refers to the amount of active drug in micrograms). The lipophilic microphase-forming material is dosed at 100 mg into a GI volume of 100 mL in the fasted state and 200 mL in the fed state. The partition coefficient of the drug between the lipophilic microphase-forming material and aqueous solution is 4000. When excess drug is dosed under these conditions, the total amount of drug dissolved at equilibrium is calculated as in the table below:

| Fed/Fasted State | Conc. Bile Salts (Vol %) | Conc. Lipophilic Microphase-forming Material (mg/mL) | Free Drug Conc. (μgA/mL) | Drug in Bile Salts (μgA/mL) | Drug in Lipophilic Microphases (μgA/mL) | Total Dissolved Drug (μgA/mL) | Fed/Fasted Ratio |
|---|---|---|---|---|---|---|---|
| Fasted | 0.5 | 0 | 1.0 | 1.0 | 0 | 2.0 | 2.5 |
| Fed | 2.0 | 0 | 1.0 | 4.0 | 0 | 5.0 | |
| Fasted | 0.5 | 1.0 | 1.0 | 1.0 | 4.0 | 6.0 | 1.2 |
| Fed | 2.0 | 0.5 | 1.0 | 4.0 | 2.0 | 7.0 | |

Thus, the use of a lipophilic microphase-forming material results in a fed/fasted ratio that is closer to 1 than when such materials are not used. This equalization of the amount of drug present in highly labile, highly mobile species between the fed and fasted states can lead to a more uniform bioavailability between the fed and fasted states.

The foregoing and other objectives, features, and advantages of the invention will be more readily understood upon consideration of the following detailed description of the invention.

DETAILED DESCRIPTION OF THE PREFERRED EMBODIMENTS

The present invention provides in one aspect a composition comprising (1) a solid adsorbate comprising a low-solubility drug adsorbed to a high surface area substrate, and (2) a lipophilic microphase-forming material. The lipophilic microphase-forming material may either be present on the adsorbate, may be mixed with the solid adsorbate, or may be separate from but co-administered with the adsorbate. The compositions may optionally include a concentration-enhancing polymer. Suitable drugs, lipophilic microphase-forming materials, adsorbates, optional concentration-enhancing polymers, and methods for making the compositions, are discussed in more detail below.

The Drug

The term "drug" is conventional, denoting a compound having beneficial prophylactic and/or therapeutic properties when administered to an animal, especially humans. Preferably, the drug is a "low-solubility drug," meaning that the drug has a minimum aqueous solubility at physiologically relevant pH (e.g., pH 1-8) of about 0.5 mg/mL or less. The invention finds greater utility as the aqueous solubility of the drug decreases. Thus, compositions of the present invention are preferred for low-solubility drugs having an aqueous solubility of less than about 0.1 mg/mL, more preferred for low-solubility drugs having an aqueous solubility of less than about 0.05 mg/mL, and even more preferred for low-solubility drugs having an aqueous solubility of less than 0.01 mg/mL. In general, it may be said that the drug has a dose-to-aqueous solubility ratio greater than about 10 mL, and more typically greater than about 100 mL, where the aqueous solubility (mg/mL) is the minimum value observed in any physiologically relevant aqueous solution (e.g., those with pH values between 1 and 8) including USP simulated gastric and intestinal buffers, and dose is in mg. Thus, a dose-to-aqueous solubility ratio may be calculated by dividing the dose (in mg) by the aqueous solubility (in mg/mL).

The drug does not need to be a low-solubility drug in order to benefit from this invention, although low-solubility drugs represent a preferred class for use with the invention. Even a drug that nonetheless exhibits appreciable aqueous solubility in the desired environment of use can benefit from the increased solubility/bioavailability made possible by this invention if it reduces the size of the dose needed for therapeutic efficacy or increases the rate of drug absorption in cases where a rapid onset of the drug's effectiveness is desired. In such cases, the drug may have an aqueous solubility up to about 1 to 2 mg/mL, or even as high as about 20 to 40 mg/mL.

In addition, the invention finds utility when the drug has a relatively high absorption rate constant. By "absorption rate constant" is meant a constant that describes the rate at which the drug is moved from the site of administration (e.g., the GI tract of an animal) to the extra-cellular compartment of the body. Absorption rate constants are generally described by zero-order or first-order models. See for example, Remington's *The Science and Practice of Pharmacy*, 20$^{th}$ Ed (2000). The invention finds particular utility when the drug has an absorption rate constant of at least 0.005 min$^{-1}$, more utility when the drug has an absorption rate constant of at least 0.01 min$^{-1}$, and even more utility when the drug has an absorption rate constant of at least 0.03 min$^{-1}$ or higher.

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, anti-atherosclerotic agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, and cholesteryl ester transfer protein inhibitors.

Each named drug should be understood to include any pharmaceutically acceptable forms of the drug. By "pharmaceutically acceptable forms" is meant any pharmaceutically acceptable derivative or variation, including stereoisomers, stereoisomer mixtures, enantiomers, solvates, hydrates, isomorphs, polymorphs, neutral forms, salt forms and prodrugs. Specific examples of antihypertensives include prazosin, nifedipine, amlodipine besylate, trimazosin and doxazosin; specific examples of a blood glucose-lowering agent are glipizide and chlorpropamide; a specific example of an anti-impotence agent is sildenafil and sildenafil citrate; specific examples of antineoplastics include chlorambucil, lomustine and echinomycin; a specific example of an imidazole-type antineoplastic is tubulazole; a specific example of an anti-hypercholesterolemic is atorvastatin calcium; specific examples of anxiolytics include hydroxyzine hydrochloride and doxepin hydrochloride; specific examples of anti-inflammatory agents include betamethasone, prednisolone, aspirin, piroxicam, valdecoxib, carprofen, celecoxib, flurbiprofen and (+)-N-{4-[3-(4-fluorophenoxy)phenoxy]-2-cyclopenten-1-yl}-N-hyroxyurea; a specific example of a barbiturate is phenobarbital; specific examples of antivirals include acyclovir, nelfinavir, and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethyl-phenoxy)-pyridin-4-yl]-(1-ethylpropyl)-amine, 3,5-dimethyl-4-(3'-pentoxy)-2-(2',4',6'-trimethylphenoxy)pyridine, pyroxidine, fluoxetine, paroxetine, venlafaxine and sertraline; specific examples of antibiotics include carbenicillin indanyl-sodium, bacampicillin hydrochloride, troleandomycin, doxycyline hyclate, ampicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, decarboethoxyloratadine and cinnarizine; specific examples of antipsychotics include ziprasidone, olanzepine, thiothixene hydrochloride, fluspirilene, risperidone and penfluridole; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalaprilic acid and lisinopril; specific examples of tetracycline antibiotics include oxytetracycline and minocycline; specific examples of macrolide antibiotics include erythromycin, clarithromycin, and spiramycin; a specific example of an azalide antibiotic is azithromycin; specific examples of glycogen phosphorylase inhibitors include [R-(R'S')]-5-chloro-N-[2-hydroxy-3-{methoxymethylamino}-3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide; and specific examples of cholesteryl ester transfer protein (CETP) Inhibitors include [2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, [2R,4S] 4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R, 4S] 4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester, (2R)-3-[[3-(4-chloro-3-ethylphenoxy)phenyl][[3-(1,1,2,2-tetrafluoroethoxy)phenyl]methyl]amino]-1,1,1-trifluoro-2-propanol, the drugs disclosed in commonly owned U.S. patent application Ser. Nos. 09/918,127 and 10/066,091, both of which are incorporated herein by reference in their entireties for all purposes, and the drugs disclosed in the following patents and published applications: DE 19741400 A1; DE 19741399 A1; WO 9914215 A1; WO 9914174; DE 19709125 A1; DE 19704244 A1; DE 19704243 A1; EP 818448 A1; WO 9804528 A2; DE 19627431 A1; DE 19627430 A1; DE 19627419 A1; EP 796846 A1; DE 19832159; DE 818197; DE 19741051; WO 9941237 A1; WO 9914204 A1; WO 9835937 A1; JP 11049743; WO 200018721; WO 200018723; WO 200018724; WO 200017164; WO 200017165; WO 200017166; EP 992496; and EP 987251, all of which are hereby incorporated by reference in their entireties for all purposes.

In a preferred embodiment, the drug is a lipophilic drug. The inventors have recognized this subclass of drugs that are essentially aqueous insoluble, highly hydrophobic, and are characterized by a set of physical properties. This subclass exhibits dramatic enhancements in aqueous concentration and bioavailability when formulated as compositions of the present invention.

The first property of this subclass of essentially insoluble, hydrophobic drugs is extremely low aqueous solubility. By "extremely low aqueous solubility" is meant that the minimum aqueous solubility at physiologically relevant pH (pH of 1 to 8) is less than about 10 μg/ml and preferably less than about 1 μg/ml.

A second property is a very high dose-to-solubility ratio. Extremely low aqueous solubility often leads to poor or slow absorption of the drug from the fluid of the gastrointestinal tract, when the drug is dosed orally in a conventional manner. For extremely low solubility drugs, poor absorption generally becomes progressively more difficult as the dose (mass of drug given orally) increases. Thus, a second property of this subclass of essentially insoluble, hydrophobic drugs is a very high dose (in mg) to aqueous solubility (in mg/ml) ratio (ml). By "very high dose-to-aqueous solubility ratio" is meant that the dose-to-aqueous solubility ratio has a value of at least 1000 ml, and preferably at least 5,000 ml, and more preferably at least 10,000 ml.

A third property of this subclass of essentially insoluble, hydrophobic drugs is that they are extremely hydrophobic. By extremely hydrophobic is meant that the Log P value of the drug, has a value of at least 4.0, preferably a value of at least 5.0, and more preferably a value of at least 5.5. Log P, defined as the base 10 logarithm of the ratio of the drug solubility in octanol to the drug solubility in water, is a widely accepted measure of hydrophobicity. Log P may be measured experimentally or calculated using methods known in the art. Calculated Log P values are often referred to by the calculation method, such as Clog P, Alog P and Mlog P.

Primarily, as a consequence of some or all of these properties, drugs of this subclass typically have very low absolute bioavailabilities. Specifically, the absolute bioavailability of drugs in this subclass when dosed orally in their undispersed state is typically less than about 10% and more often less than about 5%.

Lipophilic Microphase-Forming Materials

The lipophilic microphase-forming material may comprise a surfactant and/or a lipophilic material. Thus, as used herein, the "lipophilic microphase-forming material" is intended to include a single material as well as two or more materials. The lipophilic microphase-forming material must (1) be water immiscible (2) be capable of forming a plurality of small lipophilic microphases in the use environment and (3) have a relatively high partition coefficient for the drug in the use environment.

The lipophilic microphase-forming material must be "water immiscible," meaning that the material when administered as prescribed herein to an in vivo aqueous use environment exceeds its solubility as solvated molecules thus requiring the formation of a second phase. Ideally such a second phase takes the form of a large number of small phases such as micelles or a microemulsion. In many cases the lipophilic microphase-forming material has a critical micelle concentration ("CMC"), defined as the aqueous concentration above which micelles form. In such cases, the lipophilic microphase-forming material is present at a concentration above the CMC, thus leading to the formation of micelles. The lipophilic microphase is a separate phase in the aqueous use environment; the separate phase ranging from extremely small aggregates such as micelles or as large droplets up to a few microns in size. The lipophilic microphase-forming material also is capable of forming a plurality of small lipophilic microphases in an in vivo aqueous use environment without the need for stirring, agitation or other mechanical energy. The material need not be self-emulsifying. Nevertheless, preferably the lipophilic microphase-forming material should not agglomerate into a single phase within the use environment, but should remain as a plurality of microphases for at least 1 hour and preferably longer. When the composition is administered to an in vitro aqueous use environment, the lipophilic microphase-forming material should form a plurality of microphases with at most only slight agitation of the use environment. The microphases remain small for at least 1 hour, and more preferably at least 4 hours, after administration to the use environment.

It should be noted that some lipophilic materials that do not form a plurality of microphases when administered alone may often form such phases when administered with the drug/substrate adsorbate and optional concentration-enhancing polymer.

The resulting lipophilic microphases formed in the aqueous use environment are preferably small. By "small" is meant that the lipophilic microphase-forming material forms lipophilic microphases that are generally less than about 100 µm in characteristic diameter. By "characteristic diameter" is meant the volume average diameter of the microphase in the use environment. The characteristic diameter may be determined by standard measurement techniques, such as dynamic light scattering and static light scattering, or by examination via optical- or scanning-election microscopy, transmission-electron microscopy, coulter-counting methods, and size-exclusion field-flow fractionation. The resulting particles may be smaller, such as less than about 10 µm in characteristic diameter, less than about 1 µm in characteristic diameter, less than about 100 nm in characteristic diameter, and less than about 50 nm in characteristic diameter. In some instances, a portion of the lipophilic microphase-forming material may form small microphases, with the remaining material being present as larger microphases. When there is such a distribution in sizes, it is preferred that at least a substantial portion of the lipophilic microphase-forming material be present in small microphases. By "substantial portion" is meant that about 10 vol % or more of the material is present in small microphases. Preferably about 15 vol % or more, more preferably about 20 vol % or more of the material is present in small microphases.

The size of the microphases depends on the other components of the composition, such as the drug and polymer, the manner in which the components of the composition are combined, (such as having the lipophilic microphase-forming material adsorbed to the drug/substrate adsorbate), as well as the components of the use environment. This is particularly true in an in vivo use environment where the presence of proteins, bile salts, and other surface-active agents may cause some compositions to form suitably small lipophilic microphases even though they do not form such microphases in in vitro tests. In addition, it is well known that, in the in vivo environment, many lipophilic microphase-forming materials such as mono-, di-, and triglycerides may undergo chemical conversion to other species that in time form the microphases. Thus the ultimate test of an appropriate lipophilic microphase-forming material and composition is best conducted in the in vivo use environment.

The lability of a drug from the free drug phase into and out of the lipophilic microphase is generally a function of the microphase size. By "lability" is meant the kinetics or rate of drug release or drug partitioning into or out of the microphase. Generally, for a given mass of lipophilic microphase-forming material, lability increases as the size of the microphase decreases. As the aqueous solubility of the drug decreases, it is preferable for the characteristic size of the microphase to be smaller. Thus, when the aqueous solubility of the drug is extremely low, such as about 1 µg/ml or less, preferred compositions generally form microphases less than about 1 µm in characteristic diameter when dosed to the in vivo use environment.

The microphases may also increase the rate of drug absorption in the GI tract. Without wishing to be bound by any theory or mechanism of action, it is believed that the microphases can increase the transport rate of the drug through the unstirred water layer adjacent to the intestinal wall. As described below, the drug has a high partition coefficient in the lipophilic microphase-forming material, resulting in a high concentration of drug in the microphases. Thus, when the microphases are transported across the unstirred water layer, a large amount of drug is transported as well. Generally, the smaller the size of the microphases, the higher the rate of transport across the unstirred water layer. Once transported through the unstirred water layer, the high lability of drug in the lipophilic microphase-forming material allows the concentration of free drug at the intestinal wall to be maintained at a higher concentration than if the lipophilic microphase-forming material was not present. As a result, absorption is increased.

The drug should also have a relatively high partition coefficient in the lipophilic microphase-forming material. By partition coefficient is meant the ratio of the concentration of drug present in the lipophilic microphases to the free drug concentration as follows:

$$K_p = \frac{[\text{Drug}]_{lipophile}}{[\text{Drug}]_{free}} \quad (I)$$

where $K_p$ is the partition coefficient, $[\text{Drug}]_{lipophile}$ is the concentration of the drug in the lipophilic microphases, and $[\text{Drug}]_{free}$ is the free drug concentration.

In a given volume of the aqueous use environment, the total amount of drug in the lipophilic microphases is also dependent on the amount of lipophilic microphase present. Thus the concentration of drug in the lipophilic microphase per unit volume of the aqueous use environment, $[Drug]_{aqueous,lipophile}$, is given by:

$$[Drug]_{aqueous,lipophile} = X_{lipophile} \cdot K_p \cdot [Drug]_{free}$$

where $X_{lipophile}$ is the volume fraction of the lipophilic microphase in the use environment.

In situations where the drug is only present as free drug and drug within the lipophilic microphase, the total dissolved drug concentration $[Drug]_{aqueous,total}$ is given by:

$$[D]_{aqueous,total} = [Drug]_{free} + [Drug]_{aqueous,lipophile} \quad (II)$$

$$[Drug]_{aqueous,total} = [Drug]_{free} \cdot [1 + X_{lipophile} \cdot K_p]$$

In order for the presence of the lipophile to have a large impact on the bioavailability of a composition, there generally must be a significant fraction of the total drug dosed that is within the lipophilic microphase. By significant fraction it is generally meant that at least about 0.1% and preferably at least about 1% of the total drug dosed is present in the use environment within the lipophilic microphase-forming material. According to the above equations, the fraction of the total drug present within the lipophilic microphases generally increases with: (1) increasing $K_p$, (2) increasing $X_{lipophile}$, and (3) increasing $[Drug]_{free}$.

Since there are practical limits to the size of oral dosage forms that may be administered, it is generally undesirable to have large values of $X_{lipophile}$. For example, when the compositions of the present invention are formed into an oral tablet or capsule for administration, the mass of the tablet or capsule is generally less than about 1000 mg and preferably less than about 700 mg. Since a significant portion of the dosage form must also comprise the active drug and other excipients, the maximum amount of lipophilic microphase-forming material in a single oral dosage form is about 500 mg. When dosed orally to the GI tract of a human, the aqueous volume into which the lipophilic microphase-forming material composition disperses is generally about 50 ml up to about 500 ml, depending on the fed state of the subject. Thus, the maximum practical value for $X_{lipophile}$ is about 0.001 to 0.01. Thus, for example, when the dose of the drug is 100 mg, it is desirable to have at least 0.1 wt % (0.1 mg) and preferably at least 1 wt % (1 mg) of the drug be present in the lipophilic microphase-forming material. This generally means that the concentration of drug in the lipophilic microphase-forming material (in wt %) when the composition is dosed orally to a human is at least about 0.1 mg/500 mg or 0.02 wt % and preferably at least about 0.2 wt % (1 mg/500 mg).

The drug should have a relatively high partition coefficient in the lipophilic microphase-forming material. Preferably, the partition coefficient is about 10 or more, more preferably about 50 or more, even more preferably about 100 or more, and most preferably about 500 or more. Generally, the lower the aqueous solubility of a drug, the higher the partition coefficient should be to have a large impact on bioavailability. Thus, the partition coefficient may be greater than about 1000, greater than about 5000, greater than about 10,000, and in some cases greater than about 50,000 or more. For drugs with very low aqueous solubilities, the partition coefficient may be greater than about 100,000 or even greater than about 1,000,000 or more.

In one aspect, the minimum $K_p$ may be determined by determining the $K_p$ necessary to achieve the desired concentration of drug in the lipophilic microphase forming material.

Since the concentration of drug in the lipophilic microphase-forming material at equilibrium is given by:

$$[Drug]_{lipophile} = [Drug]_{free} \cdot K_p$$

then the minimum $K_p$ may be determined by setting the free drug concentration, $[Drug]_{free}$, to the aqueous solubility of the drug, $S_{xtal}$. The aqueous solubility, $S_{xtal}$, is the aqueous solubility of the thermodynamically most stable crystalline form of the drug, or the unadsorbed amorphous form if the crystalline form is unknown, over the pH range of 6 to 8. Using the desired concentration of drug in the lipophilic microphase-forming material given above, then the minimum $K_p$ should generally be at least about $0.02/S_{xtal}$, where $S_{xtal}$ is measured in wt %. Preferably, $K_p$ is greater than about $0.2/S_{xtal}$, more preferably greater than about $0.5/S_{xtal}$, even more preferably greater than about $1/S_{xtal}$, and most preferably greater than about $2/S_{xtal}$. Thus, when the aqueous solubility of the drug in the pH range of 6 to 8 is about 10 μg/ml or about 0.001 wt %, then $K_p$ should be greater than about 20 (0.02 wt %/0.001 wt %), preferably greater than about 200 (0.2 wt %/0.001 wt %), more preferably greater than about 500 (0.5 wt %/0.001 wt %), even more preferably greater than 1000 (1 wt %/0.001 wt %), and most preferably greater than 2000 (2 wt %/0.001 wt %).

Generally, it is preferred that the lower the mass of lipophilic microphase-forming material in the composition, the higher the partition coefficient so as to have a large impact on bioavailability. In one aspect, it is preferred that the compositions satisfy the following equation:

$$M_{lipophile} * K_p \geq 5,$$

where $M_{lipophile}$ is the mass of lipophile in the composition in grams. Preferably, $M_{lipophile} * K_p \geq 10$, more preferably $M_{lipophile} * K_p \geq 50$, and most preferably $M_{lipophile} * K_p \geq 100$. For example, as discussed above, the maximum amount of lipophilic microphase-forming material in a single oral dosage form is about 500 mg, or 0.5 gm. Thus, a composition containing 0.5 gm of a lipophilic microphase-forming material should have a partition coefficient of 10 or more, preferably 20 or more, more preferably 100 or more, and most preferably 200 or more.

The partition coefficient $K_p$ for a drug in a particular lipophilic microphase-forming material may be determined by any method or series of experiments in which the concentration of drug present as free drug and drug present in lipophilic microphases can be determined. One exemplary method is as follows. Crystalline drug (or amorphous drug if the crystalline form of the drug is not known) is added to an appropriate buffer solution such as phosphate buffered saline (PBS) (described below) at an amount such that if all of the drug dissolved the concentration would be greater than the equilibrium aqueous solubility of the drug. The concentration of free drug in the solution is then determined by any technique that can quantitatively measure the amount of dissolved drug in solution, such as high-performance liquid chromatography (HPLC) or nuclear magnetic resonance (NMR) spectroscopy. Typically, this is accomplished by collecting a sample of the solution containing the drug and either filtering or centrifuging the sample to remove undissolved drug species, and then analyzing the concentration of the remaining dissolved drug. This technique provides the value of $[Drug]_{free}$ in Equation I. Next, crystalline drug is added to an appropriate buffer solution to which various amounts of the lipophilic microphase-forming material had been added, such as 1 vol %, 2 vol % and 3 vol %, again at an amount such that if all of the drug dissolved the concentration of drug either present as free drug or in the lipophilic microphase would be greater than the equilibrium aqueous solubility of the drug with the lipophilic microphase-forming material present. The total concentration of total dissolved drug, that is the sum of drug present as free drug plus drug present in lipophilic microphases, (as given in Equation II)—is determined using the same techniques described above. The total dissolved drug concentration [Drug]$_{aqueous,total}$ is then plotted versus the vol % lipophilic microphase-forming material in the solution. The slope of the line for this graph is equal to the product of the free drug concentration (which is normally assumed to be equal to the aqueous solubility of the drug in the absence of the lipophilic microphase-forming material, or $S_{xtal}$) and $K_p$. Thus, $K_p$=slope/$S_{xtal}$. When the aqueous solubility of the lipophilic microphase-forming material or the "critical micelle concentration" (CMC) of the lipophilic microphase-forming material is very small relative to the amount of lipophilic microphase-forming material used in the above experiment, the y-intercept of the line through the data points is approximately equal to the crystalline drug aqueous solubility, $S_{xtal}$. When the amount of lipophilic microphase-forming material used is only slightly larger than the CMC or the lipophilic microphase-forming material aqueous solubility, then the values of $X_{lipophile}$ should be corrected by subtracting the CMC or solubility from the total volume fraction of lipophilic microphase-forming material added to the solution.

In one embodiment of this invention, the lipophilic microphase-forming material is part of the drug/substrate adsorbate. In such cases, it is preferred that the adsorbate comprise no greater than 50 wt % lipophilic microphase-forming material, preferably no greater than 40 wt %, more preferably no greater than 30 wt %.

Another embodiment of the present invention is a solid oral dosage form comprising the novel compositions. The solid dosage form may take the form of one or more tablets or capsules or a multiplicity of particles or granules. When the solid dosage form is one or more tablets or capsules, the dosage form may be taken orally by swallowing whole, chewed and then swallowed, or the dosage form may disintegrate and optionally dissolve in the mouth and then be swallowed. When the solid dosage form is a multiplicity of small particles or granules the powder or granules may be ingested by any known method, including first dispersing in an aqueous vehicle and then swallowing, or mixing with food and then ingesting along with the food.

In order for the compositions of the present invention to be efficiently formed into solid dosage forms it is generally desirable for the lipophilic microphase-forming materials to have relatively high melting points and relatively high $T_g$ values. However, even lipophilic microphase-forming materials that are liquid at room temperature may be formed into solid dosage forms as long as the amount incorporated into the dosage form is not too high.

When the lipophilic microphase-forming material is either a liquid at room temperature or becomes liquid at a temperature of about 50° C. or less, a preferred embodiment is to disperse the lipophilic microphase-forming material in a solid excipient. The lipophilic microphase-forming material may be adsorbed to the surface of a solid material such as microcrystalline cellulose; silica; dibasic calcium phosphate; calcium silicate (Zeodor™); clays, such as kaolin (hydrated aluminum silicate), bentonite (hydrated aluminum silicate), hectorite and Veegum®; Na-, Al-, and Fe-montmorillonite; silicon dioxide (Cab-O-Sil® or Aerosil®); magnesium trisilicate; aluminum hydroxide; magnesium hydroxide, magnesium oxide or talc. Highly porous materials such as calcium silicate are preferred. This embodiment has the advantage of separating the lipophilic microphase-forming material from the drug/substrate adsorbate, thus minimizing the effect of the lipophilic microphase-forming material on the stability of the adsorbate.

Alternatively, the lipophilic microphase-forming material may be dispersed in a water soluble or water dispersible polymer, as either a separate phase, or homogeneously distributed throughout the polymer. In one preferred embodiment, the lipophilic microphase-forming material is dispersed in a concentration-enhancing polymer. Such lipophilic microphase-forming material dispersions serve to (1) render the lipophilic microphase-forming material solid to aid in incorporation into solid dosage forms, (2) aid in dispersing of the lipophilic microphase-forming material as a microphase, and (3) provide concentration-enhancing polymer for generating and sustaining high concentrations of dissolved drug. In an often particularly preferred embodiment, the lipophilic microphase-forming material is adsorbed, along with the drug, to a high surface area substrate. Such lipophilic microphase-forming material adsorbates are often preferred even when the lipophilic microphase-forming material is a solid below about 50° C.

The lipophilic microphase-forming material may be either hydrophobic, amphiphilic, or a mixture of a hydrophobic and an amphiphilic material. By "amphiphilic" material is meant a material that has both hydrophobic and hydrophilic portions. Since hydrophobic materials alone tend not to form small microphases in an aqueous use environment, amphiphilic and mixtures of amphiphilic and hydrophobic materials are preferred. However, it is known that some such hydrophobic materials will form microphases due to the influence of (1) other excipients such as the concentration-enhancing polymer, (2) the drug itself, or (3) naturally occurring components of the GI tract. Thus, hydrophobic materials alone form a part of the invention as long as they form suitably small microphases when the compositions or dosage forms are administered to a use environment. The use of a mixture of hydrophobic and amphiphilic material may be preferred because the hydrophobic material often provides a higher partition coefficient, while the amphiphilic material may limit or reduce the size of the lipophilic microphases in the use environment. Thus, such mixtures may have higher lability and higher partition coefficients.

Generally, the lipophilic microphase-forming materials have a molecular weight of less than about 20,000 daltons. However, most lipophilic microphase-forming materials have molecular weights below about 2,000 daltons. Additionally, the lipophilic microphase-forming materials are water immiscible and form lipophilic microphases. The lipophilic microphase-forming material is therefore distinct from the concentration-enhancing polymer. The concentration-enhancing polymers generally have molecular weights of greater than about 10,000 daltons, are more soluble or dispersible in the use environment, and are generally less hydrophobic.

Examples of amphiphilic materials suitable for use as the lipophilic microphase-forming material include: sulfonated hydrocarbons and their salts, such as sodium 1,4-bis(2-ethylhexyl) sulfosuccinate, also known as docusate sodium (CROPOL) and sodium lauryl sulfate (SLS); polyoxyethylene alkyl ethers (CREMOPHOR A, BRIJ); polyoxyethylene sorbitan fatty acid esters (polysorbates, TWEEN); short-chain glyceryl mono-alkylates (HODAG, IMWITOR, MYRJ); polyglycolized glycerides (GELUCIREs); mono- and di-alkylate esters of polyols, such as glycerol; nonionic surfactants such as polyoxyethylene 20 sorbitan monooleate, (polysorbate 80, sold under the trademark TWEEN 80, available commercially from ICI); polyoxyethylene 20 sorbitan monolaurate (Polysorbate 20, TWEEN 20); polyoxyethylene (40 or 60) hydrogenated castor oil (available under the trademarks CREMOPHOR® RH40 and RH60 from BASF); polyoxyethylene (35) castor oil (CREMOPHOR® EL); polyethylene (60) hydrogenated castor oil (Nikkol HCO-60); alpha tocopheryl polyethylene glycol 1000 succinate (Vitamin E TPGS); glyceryl PEG 8 caprylate/caprate (available commercially under the registered trademark LABRASOL® from Gattefosse); PEG 32 glyceryl laurate (sold commercially under the registered trademark GELUCIRE 44/14 by Gattefosse), polyoxyethylene fatty acid esters (available commercially under the registered trademark MYRJ from ICI), polyoxyethylene fatty acid ethers (available commercially under the registered trademark BRIJ from ICI). Alkylate esters of polyols may be considered amphiphilic or hydrophobic depending on the number of alkylates per molecule and the number of carbons in the alkylate. When the polyol is glycerol, mono- and di-alkylates are often considered amphiphilic while trialkylates of glycerol are generally considered hydrophobic. However, some scientists classify even medium chain mono- and di-glycerides as hydrophobic. See for example Patel et al U.S. Pat. No. 6,294,192 (B1), which is incorporated herein in its entirety by reference. Regardless of the classification, compositions comprising mono- and di-glycerides are preferred compositions of this invention. Other suitable amphiphilic materials may be found in Patel, U.S. Pat. No. 6,294,192 and are listed as "hydrophobic non-ionic surfactants and hydrophilic ionic surfactants."

It should be noted that some amphiphilic materials may not be water immiscible by themselves, but instead are at least somewhat water soluble. Such amphiphilic materials may nevertheless be used in mixtures to form the lipophilic microphase, particularly when used as mixtures with hydrophobic materials.

Examples of hydrophobic materials suitable for use as the lipophilic microphase-forming material include: medium-chain glyceryl mono-, di-, and tri-alkylates (CAPMUL MCM, MIGLYOL 810, MYVEROL 18-92, ARLACEL 186, fractionated coconut oil, light vegetable oils); sorbitan esters (ARLACEL 20, ARLACEL 40); long-chain fatty alcohols (stearyl alcohol, cetyl alcohol, cetostearyl alcohol); long-chain fatty-acids (stearic acid); and phospholipids (egg lecithin, soybean lecithin, vegetable lecithin, and 1,2-diacyl-sn-glycero-3-phosphocholine, such as 1-palmitoyl-2-oleyl-sn-glycero-3-phosphocoline, 1,2-dipalmitoyl-sn-glycero-3-phosphocholine, 1,2-distearoyl-sn-glycero-3-phosphocholine, 1-plamitoyl-2-stearoyl-sn-glycero-3-phosphocholine, and other natural or synthetic phosphatidyl cholines); mono and diglycerides of capric and caprylic acid under the following registered trademarks: Capmul® MCM, MCM 8, and MCM 10, available commercially from Abitec, and Imwitor® 988, 742 or 308, available commercially from Condea Vista; polyoxyethylene 6 apricot kernel oil, available under the registered trademark Labrafil® M 1944 CS from Gattefosse; polyoxyethylene corn oil, available commercially as Labrafil® M 2125; propylene glycol monolaurate, available commercially as Lauroglycol from Gattefosse; propylene glycol dicaprylate/caprate available commercially as Captex® 200 from Abitec or Miglyol® 840 from Condea Vista, polyglyceryl oleate available commercially as Plurol oleique from Gattefosse, sorbitan esters of fatty acids (e.g., Span® 20, Crill® 1, Crill® 4, available commercially from ICI and Croda), and glyceryl monooleate (Maisine, Peceol); medium chain triglycerides (MCT, C6-C12) and long chain triglycerides (LCT, C14-C20) and mixtures of mono-, di-, and triglycerides, or lipophilic derivatives of fatty acids such as esters with alkyl alcohols; fractionated coconut oils, such as Miglyol® 812 which is a 56% caprylic (C8) and 36% capric (C10) triglyceride, Miglyol® 810 (68% C8 and 28% C10), Neobee® M5, Captex® 300, Captex® 355, and Crodamol® GTCC; (Miglyols are supplied by Condea Vista Inc. (Huls), Neobee® by Stepan Europe, Voreppe, France, Captex by Abitec Corp., and Crodamol by Croda Corp); vegetable oils such as soybean, safflower, corn, olive, cottonseed, arachis, sunflower seed, palm, or rapeseed; fatty acid esters of alkyl alcohols such as ethyl oleate and glyceryl monooleate. Other hydrophobic materials suitable for use as the lipophilic microphase-forming material include those listed in Patel, U.S. Pat. No. 6,294,192 as "hydrophobic surfactants." Exemplary classes of hydrophobic materials include: fatty alcohols; polyoxyethylene alkylethers; fatty acids; glycerol fatty acid monoesters; glycerol fatty acid diesters; acetylated glycerol fatty acid monoesters; acetylated glycerol fatty acid diesters, lower alcohol fatty acid esters; polyethylene glycol fatty acid esters; polyethylene glycol glycerol fatty acid esters; polypropylene glycol fatty acid esters; polyoxyethylene glycerides; lactic acid derivatives of monoglycerides; lactic acid derivatives of diglycerides; propylene glycol diglycerides; sorbitan fatty acid esters; polyoxyethylene sorbitan fatty acid esters; polyoxyethylene-polyoxypropylene block copolymers; transesterified vegetable oils; sterols; sterol derivatives; sugar esters; sugar ethers; sucroglycerides; polyoxyethylene vegetable oils; polyoxyethylene hydrogenated vegetable oils; reaction products of polyols and at least one member of the group consisting of fatty acids, glycerides, vegetable oils, hydrogenated vegetable oils, and sterols; and mixtures thereof. Mixtures of relatively hydrophilic materials, such as those termed herein as "amphiphilic" or in Patel as "hydrophilic surfactants" and the above hydrophobic materials are particularly suitable. Specifically, the mixtures of hydrophobic surfactants and hydrophilic surfactants disclosed by Patel are suitable and for many compositions, preferred. However, unlike Patel, mixtures that include triglycerides as a hydrophobic component are also suitable.

In one embodiment, the lipophilic microphase-forming material is selected from the group consisting of polyglycolized glycerides (GELUCIREs); polyoxyethylene (40 or 60) hydrogenated castor oil (available under the trademarks CREMOPHOR® RH40 and RH60 from BASF); polyoxyethylene (35) castor oil (CREMOPHOR® EL); polyethylene (60) hydrogenated castor oil (Nikkol HCO-60); alpha tocopheryl polyethylene glycol 1000 succinate (Vitamin E TPGS); glyceryl PEG 8 caprylate/caprate (available commercially under the registered trademark LABRASOL® from Gattefosse); PEG 32 glyceryl laurate (sold commercially under the registered trademark GELUCIRE 44/14 by Gattefosse); polyoxyethylene fatty acid esters (available commercially under the registered trademark MYRJ from ICI); polyoxyethylene fatty acid ethers (available commercially under the registered trademark BRIJ from ICI); polyoxyethylene alkyl ethers (CREMOPHOR A, BRIJ); long-chain fatty alcohols (stearyl alcohol, cetyl alcohol, cetostearyl alcohol); long-chain fatty-acids (stearic acid); polyoxyethylene 6 apricot kernel oil, available under the registered trademark Labrafil® M 1944 CS from Gattefosse; polyoxyethylene corn oil, available commercially as Labrafil® M 2125; propylene glycol monolaurate, available commercially as Lauroglycol from Gattefosse; polyglyceryl oleate available commercially as Plurol oleique from Gattefosse; triglycerides, including medium chain triglycerides (MCT, $C_6$-$C_{12}$) and long chain triglycerides (LCT, $C_{14}$-$C_{20}$); fractionated coconut oils, such as Miglyol® 812 which is a 56% caprylic ($C_8$) and 36% capric ($C_{10}$) triglyceride, Miglyol® 810 (68% $C_8$ and 28%

$C_{10}$), Neobee® M5, Captex® 300, Captex® 355, and Crodamol® GTCC; (Miglyols are supplied by Condea Vista Inc. [Huls], Neobee® by Stepan Europe, Voreppe, France, Captex by Abitec Corp., and Crodamol by Croda Corp); vegetable oils such as soybean, safflower, corn, olive, cottonseed, arachis, sunflower seed, palm, or rapeseed; polyoxyethylene alkylethers; fatty acids; lower alcohol fatty acid esters; polyethylene glycol fatty acid esters; polyethylene glycol glycerol fatty acid esters; polypropylene glycol fatty acid esters; polyoxyethylene glycerides; lactic acid derivatives of monoglycerides; lactic acid derivatives of diglycerides; propylene glycol diglycerides; transesterified vegetable oils; sterols; sterol derivatives; sugar esters; sugar ethers; sucroglycerides; polyoxyethylene vegetable oils; polyoxyethylene hydrogenated vegetable oils; reaction products of polyols and at least one member of the group consisting of fatty acids, glycerides, vegetable oils, hydrogenated vegetable oils, and sterols; and mixtures thereof.

Especially preferred lipophilic microphase-forming materials include mixtures of polyethoxylated castor oils and medium-chain glyceryl mono-, di-, and/or tri-alkylates, (such as mixtures of CREMOPHOR RH40 and CAPMUL MCM), mixtures of polyoxyethylene sorbitan fatty acid esters and medium-chain glyceryl mono-, di-, and/or tri-alkylates, (such as mixtures of TWEEN 80 and CAPMUL MCM), mixtures of polyethoxylated castor oils and medium-chain glyceryl mono-, di-, and/or tri-alkylates, (such as mixtures of CREMOPHOR RH40 and ARLACEL 20), mixtures of sodium taurocholic acid and palmitoyl-2-oleyl-sn-glycero-3-phosphocholine and other natural or synthetic phosphatidylcholines, and mixtures of polyglycolized glycerides and medium-chain glyceryl mono-, di-, and/or tri-alkylates, (such as mixtures of Gelucire 44/14 and CAPMUL MCM).

The lipophilic microphase-forming material is present in a sufficient amount so that the combination of the drug/substrate adsorbate and lipophilic microphase-forming material provides concentration enhancement, as described more fully below. In general, the lipophilic microphase-forming material is either present in the composition or co-administered with the drug/substrate adsorbate such that the weight ratio of the lipophilic microphase-forming material to drug (hereinafter referred to as the lipophile:drug ratio) ranges from about 0.05 to about 500 (wt/wt). For solid dosage forms, the lipophile:drug ratio typically ranges from about 0.1 to about 100, and more typically from 0.2 to 50.

The optimum amount of the lipophilic microphase-forming material depends on the mass of the dose of the drug, the partition coefficient, and the aqueous solubility of the drug. The optimum mass of the lipophilic microphase-forming material increases as the mass of the dose increases. The optimum mass of the lipophilic microphase-forming material decreases as the partition coefficient increases and as the aqueous solubility increases.

Nevertheless, in general, the amount of lipophilic microphase forming material present in the composition should not be so high that the concentration of free drug obtained in the use environment is much lower than that obtained when less lipophilic microphase-forming material is combined with the drug/substrate adsorbate and is introduced to the use environment. Generally, when the amount of lipophilic microphase-forming material that is added to the composition is greater than the amount such that all of the drug introduced to the use environment is either present as free drug or is in the lipophilic microphases, then the performance, in terms of improving drug absorption, will be reduced relative to lower levels of the lipophilic microphase-forming material. Thus, it is preferred for compositions to contain less than this "maximum preferred level." Nonetheless, levels of lipophilic microphase-forming material somewhat above this level may still improve drug absorption relative to the adsorbate alone. This maximum preferred level will depend on the free drug concentration ($[Drug]_{free}$, typically given in mg/ml), the density of the lipophilic microphase-forming material ($\rho_{lipophile}$, typically given in mg/ml), and the partition coefficient ($K_p$). The maximum preferred lipophile:drug ratio is given by the following equation:

$$\text{Maximum lipophile:drug ratio} = \rho_{lipophile}/(K_p \cdot [Drug]_{free})$$

It should be noted that for some values of $K_p$ and $[Drug]_{free}$, the maximum preferred lipophile:drug ratio will be quite large. For example, when $\rho_{lipophile}=1000$ mg/mL, $K_p=100$, and $[Drug]_{free}=0.001$ mg/mL, the maximum preferred lipophile:drug ratio is calculated to be 10,000. If the drug dose is, for example 100 mg, this results in a maximum preferred lipophile dose of 1000 g. Such high doses of lipophile are impractical. Thus when the value of $K_p$ and/or $[Drug]_{free}$ are low, the maximum preferred lipophile:drug ratio may be limited by practical considerations such as the maximum dose well tolerated by the subject or the maximum practical size of the dosage form.

Adsorbates

The drug is present in the composition in the form of an adsorbate comprising a drug and a substrate. At least a major portion of the drug in the adsorbate is amorphous. The term "amorphous" indicates simply that the drug is not crystalline as indicated by any conventional method, such as by powder X-ray diffraction (PXRD) analysis in which the sharp scattering lines associated with the crystal forms of the drug are absent or reduced in magnitude or the absence of an endothermic transition at the melting point of the crystalline drug when subjected to thermal analysis. The term "a major portion" of the drug means that at least 60% of the drug is in amorphous form, rather than a crystalline form. Preferably, the drug in the adsorbate is substantially amorphous. As used herein, "substantially amorphous" means that the amount of the drug in amorphous form is at least 80%. More preferably, the drug in the adsorbate is "almost completely amorphous" meaning that the amount of drug in the amorphous form is at least 90% as measured by powder X-ray diffraction or differential scanning calorimetry ("DSC"), or any other standard quantitative measurement. Most preferably, the drug in the adsorbate is in a completely amorphous form within the detection limits of the techniques used for characterization.

The adsorbate also includes a high surface area substrate. The substrate may be any material that is inert, meaning that the substrate does not adversely interact with the drug to an unacceptably high degree and which is pharmaceutically acceptable. The substrate also has a high surface area, meaning that the substrate has a surface area of at least 20 $m^2/g$, preferably at least 50 $m^2/g$, more preferably at least 100 $m^2/g$, and most preferably at least 180 $m^2/g$. The surface area of the substrate may be measured using standard procedures. One exemplary method is by low-temperature nitrogen adsorption, based on the Brunauer, Emmett, and Teller (BET) method, well known in the art. As discussed below, the higher the surface area of the substrate, the higher the drug-to-substrate ratio that can be achieved and still maintain high concentration-enhancements and improved physical stability. Thus, effective substrates can have surface areas of up to 200 $m^2/g$, up to 400 $m^2/g$ and up to 600 $m^2/g$ or more. The substrate should also be in the form of small particles ranging in size of from about 5 nm to about 1 μm, preferably ranging in size from about 5 nm to about 100 nm. These particles may in turn form agglomerates ranging in size from 10 nm to 100 μm. The substrate is also insoluble in the process environment used to form the adsorbate. That is, where the adsorbate is formed by solvent processing, the substrate does not dissolve in the solvent. Where the adsorbate is formed by a melt or thermal process, the substrate has a sufficiently high melting point that it does not melt.

Exemplary materials which are suitable for the substrate include inorganic oxides, such as $SiO_2$, $TiO_2$, $ZnO_2$, $ZnO$, $Al_2O_3$, MgAlSilicate, CaSilicate, $AlOH_2$, zeolites, and other inorganic molecular sieves; water insoluble polymers, such as cross-linked cellulose acetate phthalate, cross-linked hydroxypropyl methyl cellulose acetate succinate, cross-linked polyvinyl pyrrolidinone, (also known as cross povidone) microcrystalline cellulose, polyethylene/polyvinyl alcohol copolymer, polyethylene polyvinyl pyrrolidone copolymer, cross-linked carboxymethyl cellulose, sodium starch glycolate, cross-linked polystyrene divinyl benzene; and activated carbons, including those made by carbonization of polymers such as polyimides, polyacrylonitrile, phenolic resins, cellulose acetate, regenerated cellulose, and rayon.

The surface of the substrate may be modified with various substituents to achieve particular interactions of the drug with the substrate. For example, the substrate may have a hydrophobic or hydrophilic surface. By varying the terminating groups of substituents attached to the substrate, the interaction between the drug and substrate may be influenced. For example, where the drug is hydrophobic, it may be desired to select a substrate having hydrophobic substituents to improve the binding of the drug to the substrate.

Generally, the interaction of drug with the substrate should be sufficiently high such that mobility of the drug in the drug/substrate adsorbate is sufficiently decreased such that the composition has improved stability, as described below. However, the drug/substrate interaction should be sufficiently low such that the drug can readily desorb from the adsorbate when it is introduced to a use environment, resulting in a high concentration of drug in solution.

The adsorbates are formed so as to form a thin layer of amorphous drug on the surface of the substrate. By "thin layer" is meant a layer that ranges in average thickness from less than one drug molecule to as many as 10 molecules. When the drug/substrate interaction is large and the average drug layer thickness, based on the ratio of the mass of drug-to-substrate surface area, is about the dimensions of one molecule, the drug layer is generally termed a "monolayer."

The adsorption of drug to the substrate may be characterized by a shift in the infra red (IR) spectra of the drug, indicating interaction of the drug with the substrate. Such interactions are generally due to London dispersion forces, dipole-dipole interactions, hydrogen bonding, electron donor-electron acceptor interactions or ionic interactions. For example, when the drug torcetrapib is adsorption as a monolayer to a silicone dioxide substrate (Cab-O-Sil M-5P), the C=O peak at about 1700 $cm^{-1}$ is shifted by 20 $cm^{-1}$ to a lower wavenumber. At higher drug loadings (that is, more than a monolayer of drug), a second peak is observed at the original C=O position for amorphous drug (that is, amorphous drug not adsorbed to a substrate). Fitting the FTIR spectra with two gaussian absorption peaks allows quantification of the relative proportion of drug adsorbed as a monolayer and that adsorbed in multiple layers.

Additionally, if the adsorbate contains more than 2 or 3 layers of drug molecules, the physical stability of the adsorbate may be compromised, since the mobility of the drug molecules furthest from the substrate is relatively high. Thus, crystallization of the drug molecules on a thick adsorbed layer may occur more rapidly than that observed for a thin adsorbed layer.

One exemplary method for forming adsorbates of the present invention is "solvent processing." Solvent processing consists of dissolution of the drug in a solvent containing the substrate followed by rapid removal of the solvent. The term "solvent" is used broadly and includes mixtures of solvents. In general, the substrate will not significantly dissolve in the solvent and remains solid throughout the process.

First, the substrate is added to a solvent that is capable of dissolving the drug. Since it is generally desirable to form adsorbate particles that are small, preferably less than about 1 to 10 μm, the solution is agitated to form a suspension of small particles of substrate suspended in the solvent. Agitation of the solution may be performed by any method that is capable of imparting sufficient energy to the solution to break up agglomerations of substrate particles. A preferred method is sonication. Other methods that may be used to break up the particles to form a suspension of substrate in the solvent include high speed mixing, and high shear mechanical mixing. The solution is agitated for a sufficient length of time so that the substrate remains suspended in the solution for at least a few minutes. Often, to ease processing, it is desirable that the substrate remain suspended for at least 60 minutes without agglomeration. However, this is not required for practice of the invention. The solvent/substrate suspension may be continuously agitated during processing to ensure the substrate remains suspended in the solvent.

The drug is added to the solvent and dissolved. The amount of drug and substrate present in the solution is chosen to yield an adsorbate having the desired ratio of drug to substrate. In general, good results may be obtained where the solution comprises from 0.1 to 2 wt % drug and from 0.1 to 5 wt % substrate. In general, it is desired to maintain the amount of solids in the solution at less than about 10 wt %, as the substrate when present at higher concentrations may clog or stick to the surfaces of the apparatus used to form the adsorbate. The weight ratio of drug to substrate is chosen such that the desired drug-layer thickness is obtained. Generally, better dissolution performance is obtained at lower drug-to-substrate ratios. However, higher drug-to-substrate weight ratios provide good performance when the substrate surface area is high. Typically, drug-to-substrate weight ratios are less than 1.0 and often less than 0.25 to obtain preferred dissolution performance.

After the substrate has been agitated and the drug has been dissolved, the solvent is rapidly removed by evaporation or by mixing with a non-solvent. Exemplary processes are spray-drying, spray-coating (pan-coating, fluidized bed coating, etc.), and precipitation by rapid mixing of the solution with $CO_2$, hexane, heptane, water of appropriate pH, or some other non-solvent. Preferably, removal of the solvent results in a solid adsorbate. To achieve this end, it is generally desirable to rapidly remove the solvent from the solution such as in a process where the solution is atomized and the drug rapidly solidifies on the substrate.

The adsorbates formed by such processes that rapidly "quench" the material, that is, bring the material from the dissolved state to the solid state very rapidly are generally preferred as they result in a material with superior physical structure and performance.

In one embodiment, the solvent is removed through the process of spray-drying. The term spray-drying is used conventionally and broadly refers to processes involving breaking up liquid mixtures into small droplets (atomization) and rapidly removing solvent from the mixture in a container (spray-drying apparatus) where there is a strong driving force for evaporation of solvent from the droplets. The strong driving force for solvent evaporation is generally provided by maintaining the partial pressure of solvent in the spray-drying apparatus well below the vapor pressure of the solvent at the temperature of the drying droplets. This is accomplished by either (1) maintaining the pressure in the spray-drying apparatus at a partial vacuum (e.g., 0.01 to 0.50 atm); (2) mixing the liquid droplets with a warm drying gas; or (3) both. In addition, at least a portion of the heat required for evaporation of solvent may be provided by heating the spray solution.

Solvents suitable for spray-drying can be water or any organic compound in which the drug is soluble and the substrate insoluble. Preferably, the solvent is also volatile with a boiling point of about 150° C. or less. In addition, the solvent should have relatively low toxicity and be removed from the adsorbate to a level that is acceptable according to The International Committee on Harmonization (ICH) guidelines. Removal of solvent to this level may require a processing step such as tray-drying subsequent to the spray-drying or spray-coating process. Preferred solvents include alcohols such as methanol, ethanol, n-propanol, isopropanol, and butanol; ketones such as acetone, methyl ethyl ketone and methyl iso-butyl ketone; esters such as ethyl acetate and propylacetate; and various other solvents such as acetonitrile, methylene chloride, toluene, and 1,1,1-trichloroethane. Mixtures, particularly mixtures of an organic solvent such as methanol, ethanol or acetone and water are often desirable. Lower volatility solvents such as dimethyl acetamide or dimethylsulfoxide can also be used. Mixtures of solvents, such as 50% methanol and 50% acetone, can also be used, as can mixtures with water as long as the drug is sufficiently soluble to make the spray-drying process practicable.

Generally, the temperature and flow rate of the drying gas is chosen so that the droplets containing the adsorbate are dry enough by the time they reach the wall of the apparatus that they are essentially solid, and so that they form a fine powder and do not stick to the apparatus wall. The actual length of time to achieve this level of dryness depends on the size of the droplets. Droplet sizes generally range from 1 µm to 500 µm in diameter, with 5 to 150 µm being more typical. The large surface-to-volume ratio of the droplets and the large driving force for evaporation of solvent leads to actual drying times of a few seconds or less, and more typically less than 0.1 second. Solidification times should be less than 100 seconds, preferably less than a few seconds, and more preferably less than 1 second. In general, to achieve this rapid solidification of the solution, it is preferred that the size of droplets formed during the spray-drying process be less than about 150 µm in diameter. The resultant solid particles thus formed are generally less than about 150 µm in diameter.

Following solidification, the solid powder typically stays in the spray-drying chamber for about 5 to 60 seconds, further evaporating solvent from the solid powder. The final solvent content of the solid adsorbate as it exits the dryer should be low, since this reduces the mobility of drug molecules in the adsorbate, thereby improving its stability. Generally, the solvent content of the adsorbate as it leaves the spray-drying chamber should be less than 10 wt % and preferably less than 2 wt %. Following spray-drying, the adsorbate may be dried in a solvent drier, such as a tray-dryer or a fluidized-bed dryer to remove residual solvents.

Spray-drying processes and spray-drying equipment are described generally in Perry's *Chemical Engineers' Handbook*, Sixth Edition (R. H. Perry, D. W. Green, J. O. Maloney, eds.) McGraw-Hill Book Co. 1984, pages 20-54 to 20-57. More details on spray-drying processes and equipment are reviewed by Marshall "Atomization and Spray-Drying," 50 *Chem. Eng. Prog. Monogr. Series* 2 (1954).

As mentioned above, preferred adsorbates of the present invention are made by processes such as spray-drying that rapidly bring the drug from the dissolved state to the solid adsorbed state. Such adsorbates have a unique physical structure and have greater physical stability and dissolution performance relative to those made by processes that slowly remove solvent.

Another method to produce adsorbates comprising amorphous drug adsorbed to a substrate is a thermal process. Here, the drug is melted and then coated onto the surface of substrates using, for example, a twin-screw extruder. In one exemplary technique the drug is first uniformly blended with the substrate. The blend may be prepared using methods well known in the art for obtaining powdered mixtures with high content uniformity. For example, the drug and substrate may first be independently milled to obtain a small particle size (e.g., less than about 100 µm) and then added to a V blender and blended for 20 minutes. This blend may then be milled to break up any agglomerates, and then blended in a V blender for an additional period of time to obtain a uniform preblend of drug and substrate.

This preblend of drug and substrate is fed into an extruder. By "extruder" is meant a device or collection of devices that creates a molten extrudate by heat and/or shear forces and/or produces a uniformly mixed extrudate. Such devices include, but are not limited to single-screw extruders; twin-screw extruders, including co-rotating, counter-rotating, intermeshing, and non-intermeshing extruders; multiple screw extruders; ram extruders, consisting of a heated cylinder and a piston for extruding the molten extrudate; gear-pump extruders, consisting of a heated gear pump, generally counter-rotating, that simultaneously heats and pumps the molten feed; and conveyer extruders. Conveyer extruders comprise a conveyer means for transporting solid and/or powdered feeds, such, such as a screw conveyer or pneumatic conveyer, and a pump. At least a portion of the conveyer means is heated to a sufficiently high temperature to produce the extrudate. Optionally, an in-line mixer may be used before or after the pump to ensure the extrudate is substantially homogeneous. In each of these extruders the composition is mixed to form a uniformly mixed extrudate. Such mixing may be accomplished by various mechanical and processing means, including mixing elements, kneading elements, and shear mixing by backflow.

In the case of a twin-screw extruder, the screw configuration and mixing paddles are set so as to provide a high degree of fill of the screw sections for efficient heat transfer from the barrel and avoidance of excessive flow restriction. The screw configuration is also selected such that there is sufficient mechanical energy (i.e., shear) to break apart any aggregated substrate still remaining after the preblend step and to uniformly mix the drug and substrates. The barrel temperature should be ramped from approximately room temperature at the feed area to slightly above the melting temperature of the drug in the last barrel zone (discharge end). This technique is applicable for any drug with a melting temperature low enough to melt in the extruder (<400° C.), and for drugs with acceptable chemical stability at the elevated temperatures. Thermal processes such as melt-extrusion processes and equipment are described generally in *Encyclopedia of Chemical Technology*, 4th Edition (John Wiley & Sons, 1991).

A processing aid may optionally be blended with such drug/substrate mixtures to form a three-component (or more) preblend that is fed to the extruder. One object of such additives is to lower the temperature required for liquefaction of the drug. Thus, the additive typically has a melt point below that of the drug and the drug is typically soluble in the molten additive. The additive may be a volatile material such as water that evaporates from the composition or it may have a high boiling point, such as a mono- or di-glyceride such that it remains part of the composition following processing.

Analogous to the solvent processing method described above, it is preferred to rapidly "quench" the molten material as it exits (is discharged from) the extruder. Any method that results in rapid solidification of the drug as a solid adsorbed layer on the substrate is suitable. Exemplary methods are contact with a cooling fluid such as a cold gas or liquid. Alternatively, the material may enter a cooled mill where heat is transferred from the material at the same time as it is milled into a fine powder with granule sizes from about 100 nm to 100 μm.

Alternatively, a solvent, such as water, can be added to the preblend fed to a twin screw extruder. The screw configuration is designed so that there is sufficient pressure in the extruder to prevent vaporization of the solvent at the temperatures required to melt the drug. When the extrudate exits the extruder, the sudden decrease in pressure causes rapid vaporization of the solvent, leading to rapid cooling and congealing of the adsorbate material. Any residual solvent in the composition can be removed using conventional drying technology such as a tray drier or a fluidized-bed drier.

Thus, preferred adsorbates of the present invention may be made by any solvent or thermal process that rapidly solidifies (that is, quenches) the material by solvent removal, precipitation with a nonsolvent or cooling. Such materials, termed "rapidly quenched adsorbates," have superior properties to adsorbates made by other methods.

In particular, when such "rapidly quenched adsorbates" are delivered to an aqueous use environment, they provide enhanced drug concentrations. Specifically, such rapidly quenched adsorbates provide a higher maximum free drug concentration or a higher maximum total dissolved drug concentration than that provided by a control, termed a "slow-evaporation control composition," formed by evaporating the solvent from a suspension of the same substrate in a solution of drug over a period of 30 minutes or more.

In addition, such rapidly quenched adsorbates may also show improved physical stability, slower crystallization rates and superior thermal properties relative to the slow-evaporation control composition.

The drug/substrate adsorbates resulting from the various preparation techniques are solid materials comprising about 5 wt % to 90 wt % drug. The materials are typically agglomerates of particles, the agglomerates having a mean diameter ranging from 10 nm to 100 μm. The agglomerates typically retain the fine particulate nature of the starting substrate. In the case of high surface area silicon dioxide, these consist of branched chains composed of many particles with mean diameters of about 10 to 30 nm, or agglomerates of very small spheres (<10 μm).

For adsorbates in which the substrate has a surface area of approximately 200 $m^2/g$, it is believed that for low drug loadings (under about 12 wt %), the drug is present primarily as drug molecules directly adsorbed onto the substrate surface. For such high surface area substrates, there is sufficient surface area for all drug to be directly adsorbed to the substrate up to a drug-to-substrate weight ratio of about 8. Drug adsorbed onto such substrates can be considered a mono layer. Drug adsorbed in this way is noncrystalline and thus may be considered amorphous. However, the interaction of the drug and substrate surface give the drug substantially different physical properties than bulk amorphous drug alone.

At greater drug loadings in the adsorbate, it is believed that the drug forms additional layers of amorphous drug on top of the initial monolayer. While not wishing to be bound by any particular theory, it is believed that the interaction of the thin layer(s) of the drug with the substrate improves the physical stability of the drug by decreasing the mobility of the drug on the substrate relative to the mobility of drug in a bulk amorphous material. This may result in improved physical stability by hindering diffusion of drug, and thus inhibiting crystal formation.

As the surface area of the substrate increases, the amount of drug that can be incorporated into the adsorbate while maintaining a monolayer (or less) of drug also increases. For example, if the substrate has a surface area of 400 $m^2/g$, the drug loading that leads to a monolayer is approximately 21 wt %, while if the substrate has a surface area of 600 $m^2/g$, the drug loading can be about 29% while maintaining a monolayer of drug on the substrate. Thus, it is desirable to use a substrate with as high a surface area as possible to obtain high drug loadings. Such values for the relationship of "drug loading" to substrate surface area are only approximate and depend on the specific size, shape, and orientation of each specific drug.

The amorphous drug adsorbed to the substrate is in a relatively high energy state when dosed to an aqueous use environment. While not wishing to be bound by any particular theory or mechanism of action, it is believed this high energy state is due to generally reduced drug-drug interactions of the drug adsorbed to the substrate compared with amorphous or crystalline drug alone. The substrate stabilizes this high-energy amorphous form of the drug. Thus, when introduced to an aqueous use environment, the drug/substrate adsorbate may provide enhanced aqueous concentration of drug.

The physical nature of this stabilized high-energy state of the amorphous drug may be characterized using IR spectroscopy. Generally, interactions of the drug with the substrate are characterized by a shift in the IR spectrum to a lower wave number, indicating hydrogen bonding of the drug to the substrate. In addition, the physical nature of the adsorbed drug may be evaluated by techniques such as vapor absorption, thermal calorimetry such as differential scanning calorimetry (DSC), or powder x-ray diffraction.

The adsorbate may also include optional additional components, in addition to the processing aids described above, such as surfactants, pH modifiers, disintegrants, binders, lubricants, etc. These materials may help improve processing, performance, or help in preparing dosage forms containing the adsorbates, as discussed below.

One particularly preferred optional additional component is a concentration-enhancing polymer. While the drug/substrate adsorbate provides enhanced concentration of drug in a use environment relative to amorphous drug alone, the inclusion of a concentration-enhancing polymer in the adsorbate may improve the observed enhancement and/or allow for sustaining the enhanced concentration for a longer period of time.

The compositions of the present invention containing concentration-enhancing polymers may be prepared through a variety of methods. The concentration-enhancing polymer may be co-adsorbed onto the substrate with the drug, so as to form an amorphous dispersion of drug and polymer adsorbed onto the substrate. Alternatively, the concentration-enhancing polymer may be combined with the drug/substrate adsorbate in a mixture.

In one preferred method for combining the adsorbate and concentration-enhancing polymer, the concentration-enhancing polymer is co-adsorbed with the drug onto the substrate. This results in an amorphous dispersion of drug and polymer adsorbed onto the surface of the substrate. The concentration-enhancing polymer may be co-adsorbed with the drug on the substrate using any method that results in a thin layer of amorphous drug and polymer adsorbed onto the surface of the substrate. The layer may range in thickness from a complete or discontinuous layer of drug and polymer molecules adsorbed directly to the substrate surface, up to a layer of drug and polymer up to a thickness of about the size of 5 to 10 polymer or drug molecules. At least a major portion of the drug present in the adsorbate is amorphous. Preferably, the drug in the adsorbate is substantially amorphous, and more preferably, the drug is almost completely amorphous. While the dispersion of drug and polymer adsorbed onto the substrate may have drug-rich domains and polymer-rich domains, in one embodiment the dispersion is substantially homogeneous, meaning that the amount of the drug present in drug-rich amorphous domains within the dispersion is less than 20%. Often, for such materials the dispersion is "completely homogeneous," meaning that the amount of drug in drug-rich domains is less than 10%.

One method for adsorbing the concentration-enhancing polymer onto the substrate with the drug is to form the adsorbate using a solvent process as described above. In that case, the concentration-enhancing polymer and drug are dissolved in a common solvent to which the substrate had been added. By "common solvent" is meant a solvent capable of dissolving both the drug and the concentration-enhancing polymer.

In one exemplary method, the substrate is first added to the common solvent and sonicated. The concentration-enhancing polymer is then added to the solution and dissolved. The drug is then added to the solvent and dissolved. The solvent is then rapidly removed from the resulting solution of dissolved drug, dissolved polymer and suspended substrate. The resulting particles of adsorbate are then collected and dried.

An alternative method to co-adsorb drug and polymer onto a substrate is using a thermal process as described above. In one exemplary method, drug, concentration-enhancing polymer, and substrate are preblended and fed to an extruder. The extruder is designed to melt the drug and polymer, resulting in adsorption onto the substrate. The composition is then rapidly cooled to form a rapidly quenched adsorbate, as described above. Additives, such as water, solvents, low-melting-point solids, or plasticizers may be added to the preblend to reduce the melting point of the polymer and allow for lower processing temperatures.

The resulting drug/polymer/substrate adsorbates may comprise from 2 wt % to 90 wt % drug, from 2 to 90 wt % substrate, and from 5 wt % to 95 wt % concentration-enhancing polymer. The mean diameter of the drug/polymer/substrate adsorbates ranges from about 5 nm to about 100 µm, and the adsorbates are typically agglomerates of particles having mean diameters of about 5 nm to 50 nm.

Concentration-Enhancing Polymers

Concentration-enhancing polymers suitable for use in the various aspects of the present invention should be pharmaceutically acceptable, and should have at least some solubility in aqueous solution at physiologically relevant pHs (e.g. 1-8). Almost any neutral or ionizable polymer that has an aqueous-solubility of at least 0.1 mg/mL over at least a portion of the pH range of 1-8 may be suitable.

It is preferred that the concentration-enhancing polymers be "amphiphilic" in nature, meaning that the polymer has hydrophobic and hydrophilic portions. Amphiphilic polymers are preferred because it is believed that such polymers tend to have relatively strong interactions with the drug and may promote the formation of various types of polymer/drug assemblies in solution. A particularly preferred class of amphiphilic polymers are those that are ionizable, the ionizable portions of such polymers, when ionized, constituting at least a portion of the hydrophilic portions of the polymer. For example, while not wishing to be bound by a particular theory, such polymer/drug assemblies may comprise hydrophobic drug clusters surrounded by the concentration-enhancing polymer with the polymer's hydrophobic regions turned inward towards the drug and the hydrophilic regions of the polymer turned outward toward the aqueous environment. Alternatively, depending on the specific chemical nature of the drug, the ionized functional groups of the polymer may associate, for example, via ion pairing or hydrogen bonds, with ionic or polar groups of the drug. In the case of ionizable polymers, the hydrophilic regions of the polymer would include the ionized functional groups. In addition, the repulsion of the like charges of the ionized groups of such polymers (where the polymer is ionizable) may serve to limit the size of the polymer/drug assemblies to the nanometer or submicron scale. Such drug/concentration-enhancing polymer assemblies in solution may well resemble charged polymeric micellar-like structures. In any case, regardless of the mechanism of action, the inventors have observed that such amphiphilic polymers, particularly ionizable cellulosic polymers such as those listed below, have been shown to interact with drug so as to maintain a higher concentration of drug in an aqueous use environment.

One class of polymers suitable for use with the present invention comprises neutral non-cellulosic polymers. Exemplary polymers include: vinyl polymers and copolymers having at least one substituent selected from the group comprising hydroxyl, alkylacyloxy, and cyclicamido; vinyl copolymers of at least one hydrophilic, hydroxyl-containing repeat unit and at least one hydrophobic, alkyl- or aryl-containing repeat unit; polyvinyl alcohols that have at least a portion of their repeat units in the unhydrolyzed (vinyl acetate) form; polyvinyl alcohol polyvinyl acetate copolymers; polyvinyl pyrrolidone; polyethylene polyvinyl alcohol copolymers, and polyoxyethylene-polyoxypropylene block copolymers (also referred to as poloxamers).

Another class of polymers suitable for use with the present invention comprises ionizable non-cellulosic polymers. Exemplary polymers include: carboxylic acid-functionalized vinyl polymers, such as the carboxylic acid functionalized polymethacrylates and carboxylic acid functionalized polyacrylates such as the EUDRAGITS® manufactured by Rohm Tech Inc., of Malden, Mass.; amine-functionalized polyacrylates and polymethacrylates; high molecular weight proteins such as gelatin and albumin; and carboxylic acid functionalized starches such as starch glycolate.

Non-cellulosic polymers that are amphiphilic are copolymers of a relatively hydrophilic and a relatively hydrophobic monomer. Examples include acrylate and methacrylate copolymers. Exemplary commercial grades of such copolymers include the EUDRAGITS, which are copolymers of methacrylates and acrylates.

A preferred class of polymers comprises ionizable and neutral (or non-ionizable) cellulosic polymers with at least one ester- and/or ether-linked substituent in which the polymer has a degree of substitution of at least 0.05 for each substituent. It should be noted that in the polymer nomenclature used herein, ether-linked substituents are recited prior to "cellulose" as the moiety attached to the ether group; for example, "ethylbenzoic acid cellulose" has ethoxybenzoic acid substituents. Analogously, ester-linked substituents are recited after "cellulose" as the carboxylate; for example, "cellulose phthalate" has one carboxylic acid of each phthalate moiety ester-linked to the polymer and the other carboxylic acid unreacted.

It should also be noted that a polymer name such as "cellulose acetate phthalate" (CAP) refers to any of the family of cellulosic polymers that have acetate and phthalate substituents attached via ester linkages to a significant fraction of the cellulosic polymer's hydroxyl groups. Generally, the degree of substitution of each substituent can range from 0.05 to 2.9 as long as the other criteria of the polymer are met. "Degree of substitution" refers to the average number of the three hydroxyls per saccharide repeat unit on the cellulose chain that have been substituted. For example, if all of the hydroxyls on the cellulose chain have been phthalate substituted, the phthalate degree of substitution is 3. Also included within each polymer family type are cellulosic polymers that have additional substituents added in relatively small amounts that do not substantially alter the performance of the polymer.

Amphiphilic cellulosics comprise polymers in which the parent cellulose polymer has been substituted at any or all of the 3 hydroxyl groups present on each saccharide repeat unit with at least one relatively hydrophobic substituent. Hydrophobic substituents may be essentially any substituent that, if substituted to a high enough level or degree of substitution, can render the cellulosic polymer essentially aqueous insoluble. Examples of hydrophobic substituents include ether-linked alkyl groups such as methyl, ethyl, propyl, butyl, etc.; or ester-linked alkyl groups such as acetate, propionate, butyrate, etc.; and ether- and/or ester-linked aryl groups such as phenyl, benzoate, or phenylate. Hydrophilic regions of the polymer can be either those portions that are relatively unsubstituted, since the unsubstituted hydroxyls are themselves relatively hydrophilic, or those regions that are substituted with hydrophilic substituents. Hydrophilic substituents include ether- or ester-linked nonionizable groups such as the hydroxy alkyl substituents hydroxyethyl, hydroxypropyl, and the alkyl ether groups such as ethoxyethoxy or methoxyethoxy. Particularly preferred hydrophilic substituents are those that are ether- or ester-linked ionizable groups such as carboxylic acids, thiocarboxylic acids, substituted phenoxy groups, amines, phosphates or sulfonates.

One class of cellulosic polymers comprises neutral polymers, meaning that the polymers are substantially non-ionizable in aqueous solution. Such polymers contain non-ionizable substituents, which may be either ether-linked or ester-linked. Exemplary ether-linked non-ionizable substituents include: alkyl groups, such as methyl, ethyl, propyl, butyl, etc.; hydroxy alkyl groups such as hydroxymethyl, hydroxyethyl, hydroxypropyl, etc.; and aryl groups such as phenyl. Exemplary ester-linked non-ionizable substituents include: alkyl groups, such as acetate, propionate, butyrate, etc.; and aryl groups such as phenylate. However, when aryl groups are included, the polymer may need to include a sufficient amount of a hydrophilic substituent so that the polymer has at least some water solubility at any physiologically relevant pH of from 1 to 8.

Exemplary non-ionizable cellulosic polymers that may be used as the polymer include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

A preferred set of non-ionizable (neutral) cellulosic polymers are those that are amphiphilic. Exemplary polymers include hydroxypropyl methyl cellulose and hydroxypropyl cellulose acetate, where cellulosic repeat units that have relatively high numbers of methyl or acetate substituents relative to the unsubstituted hydroxyl or hydroxypropyl substituents constitute hydrophobic regions relative to other repeat units on the polymer.

A preferred class of cellulosic polymers comprises polymers that are at least partially ionizable at physiologically relevant pH and include at least one ionizable substituent, which may be either ether-linked or ester-linked. Exemplary ether-linked ionizable substituents include: carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, and the various isomers of picolinic acid such as ethoxypicolinic acid, etc.; thiocarboxylic acids, such as thioacetic acid; substituted phenoxy groups, such as hydroxyphenoxy, etc.; amines, such as aminoethoxy, diethylaminoethoxy, trimethylaminoethoxy, etc.; phosphates, such as phosphate ethoxy; and sulfonates, such as sulphonate ethoxy. Exemplary ester linked ionizable substituents include: carboxylic acids, such as succinate, citrate, phthalate, terephthalate, isophthalate, trimellitate, and the various isomers of pyridinedicarboxylic acid, etc.; thiocarboxylic acids, such as thiosuccinate; substituted phenoxy groups, such as amino salicylic acid; amines, such as natural or synthetic amino acids, such as alanine or phenylalanine; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer aqueous soluble at least at pH values where any ionizable groups are ionized. In some cases, the aromatic substituent may itself be ionizable, such as phthalate or trimellitate substituents.

Exemplary cellulosic polymers that are at least partially ionized at physiologically relevant pHs include: hydroxypropyl methyl cellulose acetate succinate (HPMCAS), hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate (HPMCP), hydroxyethyl methyl cellulose acetate succinate, hydroxyethyl methyl cellulose acetate phthalate, carboxyethyl cellulose, ethylcarboxymethyl cellulose (also referred to as carboxymethylethyl cellulose or CMEC), carboxymethyl cellulose, cellulose acetate phthalate (CAP), methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate (CAT), methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate. Of these cellulosic polymers that are at least partially ionized at physiologically relevant pHs, those that the inventors have found to be most preferred are HPMCAS, HPMCP, CAP, CAT, carboxyethyl cellulose, carboxymethyl cellulose, and ethyl carboxymethyl cellulose.

Another preferred class of polymers consists of neutralized acidic polymers. By "neutralized acidic polymer" is meant any acidic polymer for which a significant fraction of the "acidic moieties" or "acidic substituents" have been "neutralized"; that is, exist in their deprotonated form. By "acidic polymer" is meant any polymer that possesses a significant number of acidic moieties. In general, a significant number of acidic moieties would be greater than or equal to about 0.1 milliequivalents of acidic moieties per gram of polymer. "Acidic moieties" include any functional groups that are sufficiently acidic that, in contact with or dissolved in water, can at least partially donate a hydrogen cation to water and thus increase the hydrogen-ion concentration. This definition includes any functional group or "substituent," as it is termed when the functional group is covalently attached to a polymer that has a pKa of less than about 10. Exemplary classes of functional groups that are included in the above description include carboxylic acids, thiocarboxylic acids, phosphates, phenolic groups, and sulfonates. Such functional groups may make up the primary structure of the polymer such as for polyacrylic acid, but more generally are covalently attached to the backbone of the parent polymer and thus are termed "substituents." Neutralized acidic polymers are described in more detail in commonly assigned U.S. patent application Ser. No. 60/300,256 entitled "Pharmaceutical Compositions of Drugs and Neutralized Acidic Polymers" filed Jun. 22, 2001, the relevant disclosure of which is incorporated by reference.

While specific polymers have been discussed as being suitable for use in the mixtures of the present invention, blends of such polymers may also be suitable. Thus the term "concentration-enhancing polymer" is intended to include blends of polymers in addition to a single species of polymer.

Preparation of Compositions

Compositions of the present invention may be prepared according to any technique that results in a mixture comprising (1) an adsorbate comprising a low-solubility drug and a high surface area substrate, wherein at least a major portion of the drug is amorphous, and (2) a lipophilic microphase-forming material. In one method, an adsorbate comprising the drug, substrate, optional concentration-enhancing polymer, and lipophilic microphase-forming material is formed so that the lipophilic microphase-forming material is co-adsorbed to the substrate along with the drug and optional concentration-enhancing polymer. Alternatively, the drug/substrate adsorbate with optional concentration-enhancing polymer may be formed and then mixed with the lipophilic microphase-forming material so that the lipophilic microphase-forming material is mixed with the adsorbate. As yet another alternative, the drug/substrate adsorbate with optional concentration-enhancing polymer may be prepared and then co-administered with a lipophilic microphase-forming material to a use environment, so that the adsorbate and lipophilic microphase-forming material are both present in the use environment.

In many cases, to aid the dispersing of the lipophilic microphase-forming material in the use environment, it is often desirable to disperse the lipophilic microphase-forming material in a water soluble or water dispersible matrix prior to forming the mixture. Alternatively, the lipophilic microphase-forming material may be adsorbed to a water insoluble substrate such as the high surface area substrates discussed above for formation of the drug adsorbate, including dibasic calcium phosphate, calcium carbonate, microcrystalline cellulose, silicon dioxide calcium silicate; clays, such as kaolin (hydrated aluminum silicate), bentonite (hydrated aluminum silicate), hectorite and Veegum®; silicon dioxide (Cab-O-Sil®) or Aerosil®); magnesium trisilicate; aluminum hydroxide; magnesium hydroxide, magnesium oxide or talc. Highly porous materials such as calcium silicate are preferred. In one embodiment, the lipophilic microphase-forming material is adsorbed to a concentration-enhancing polymer, such as those previously discussed. When the lipophilic microphase-forming material is dispersed in a water dispersible matrix, the dispersion may be formed by any of the processes described previously for forming the drug/substrate adsorbate including thermal processes such as extrusion, solvent processes such as spray-drying, as well as conventional wet and dry granulation processes. Following forming the adsorbate dispersion or granule of lipophilic microphase-forming material the dispersion or granule containing the lipophilic microphase-forming material may then be blended with the drug/substrate adsorbate.

When it is desired to adsorb (or absorb) the lipophilic microphase-forming material onto a solid substrate, the lipophilic microphase-forming material may be adsorbed onto the solid substrate using any conventional method. In one exemplary method, the substrate is initially dried to remove water. The lipophilic microphase-forming material is then combined with the substrate. The lipophilic microphase-forming material may be combined with the substrate by the use of a planetary mixer, a Z-blade mixer, a rotogranulator or similar equipment. Preferably, the amount of lipophilic microphase-forming material is kept sufficiently low so that the mixture of lipophilic microphase-forming material and solid substrate forms a free-flowing powder. The proportion of lipophilic microphase-forming material to solid substrate preferably is less than about 4:1 (wt:wt) lipophilic microphase-forming material to solid substrate. As the weight ratio of lipophilic microphase-forming material to substrate increases, the material becomes cake-like, and then oily or slurry-like. The particular ratio will depend on the porosity of the substrate and the nature of the lipophilic microphase-forming material. The lipophilic microphase-forming material may be diluted in a solvent such as methanol prior to adsorbing the lipophilic microphase-forming material to the solid substrate. The resulting slurry is dried, for example in a vacuum desiccator, to form a solid material comprising the lipophilic microphase-forming material and substrate. This solid material may then be combined with the drug/substrate adsorbate to form a composition of the present invention.

Mixing methods include convective mixing, shear mixing, or diffusive mixing. Convective mixing involves moving a relatively large mass of material from one part of a powder bed to another, by means of blades or paddles, revolving screw, or an inversion of the powder bed. Shear mixing occurs when slip planes are formed in the material to be mixed. Diffusive mixing involves an exchange of position by single particles. These mixing processes can be performed using equipment in batch or continuous mode. Tumbling mixers (e.g., twin-shell) are commonly used equipment for batch processing. Continuous mixing can be used to improve composition uniformity. Continuous mixers include "in-line" mixers and extruders. Extruders may be single screw or twin-screw. Twin-screw extruders may turn in the same or opposite direction.

Milling may also be employed to combine the adsorbate and the lipophilic microphase-forming material. Milling is the mechanical process of reducing the particle size of solids (comminution). The most common types of milling equipment are the rotary cutter, the hammer, the roller, and fluid energy mills. Equipment choice depends on the characteristics of the ingredients in the composition (e.g., soft, abrasive, or friable). Wet- or dry-milling techniques can be chosen for several of these processes, also depending on the characteristics of the ingredients (e.g. adsorbate stability in solvent). The milling process may serve simultaneously as a mixing process if the feed materials are heterogeneous. Conventional mixing and milling processes suitable for use in the present invention are discussed more fully in Lachman, et al., *The Theory and Practice of Industrial Pharmacy* (3d Ed. 1986).

The adsorbate and lipophilic microphase-forming material may also be combined by dry- or wet-granulating processes.

In another embodiment, the adsorbate and lipophilic microphase-forming material may be co-administered to the environment of use. By "co-administered" is meant that the adsorbate and lipophilic microphase-forming material are administered separately from each other to the use environment. In one embodiment, the adsorbate and lipophilic microphase-forming material are co-administered within the same general time frame as each other, such as within 60 minutes, preferably within 30 minutes, more preferably within 15 minutes of each other.

Concentration-Enhancement

The compositions of the present invention provide concentration-enhancement in a use environment relative to one or more control compositions. The compositions of the present invention may provide concentration-enhancement relative to a first control composition consisting essentially of the drug/substrate adsorbate but without any lipophilic microphase forming material present. Thus, the lipophilic microphase forming material is either present in the composition or co-administered in a sufficient amount to provide concentration enhancement (as described more fully below) relative to a first control consisting essentially of an equivalent amount of the drug/substrate adsorbate but with no lipophilic microphase forming material present. That is, the first control composition is identical to the composition comprising the drug/substrate adsorbate and the lipophilic microphase-forming material except for the absence of the lipophilic microphase-forming material.

Alternatively, the compositions of the present invention provide concentration enhancement relative to a second control composition consisting essentially of the same lipophilic microphase-forming material combined with crystalline drug in an amount equivalent to the amount of drug in the test composition, but with the drug not adsorbed to the high surface area substrate. Thus, the second control composition is identical to the composition of the invention except that the drug is in the form of crystalline drug rather than amorphous drug adsorbed to a high surface area substrate. In cases where more than one crystal form of the drug is known, the control composition consists of the crystalline form that is most thermodynamically stable at ambient conditions (25° C. and 50% relative humidity). In cases where no crystalline form of the drug is known, unadsorbed amorphous drug may be substituted for crystalline drug.

At a minimum, compositions of the present invention provide concentration enhancement in a use environment relative to at least one of the two above controls. Preferably, compositions of the present invention will provide concentration enhancement in a use environment relative to both of the above two controls.

Compositions comprising a drug/substrate adsorbate and lipophilic microphase-forming material provide concentration-enhancement in either an in vivo or in vitro use environment. In an in vivo use environment, the concentration-enhancement may result in either enhanced relative bioavailability and/or a more regular fed/fasted bioavailability ratio (that is, a fed/fasted bioavailability ratio closer to 1). In an in vitro use environment, concentration enhancement may be either enhanced drug concentration in highly mobile drug species, reduced precipitate, enhanced maximum drug concentration, or enhanced dissolution area under the concentration Versus time curve (AUC).

As used herein, a "use environment" can be either the in vivo environment of the GI tract of an animal, such as a mammal and particularly a human, or the in vitro environment of a test solution, such as phosphate buffered saline (PBS). Concentration enhancement may be determined through either in vivo tests or through in vitro dissolution tests. A composition of the present invention meets the concentration enhancement criteria in at least one of the above test environments.

In one aspect, the compositions comprising an adsorbate and lipophilic microphase-forming material provide improved relative bioavailability relative to either the first control composition, the second control composition, or preferably both. Relative bioavailability may be tested in vivo in animals or humans using conventional methods for making such a determination. An in vivo test, such as a crossover study, may be used to determine whether a test composition provides an enhanced relative bioavailability compared with one or both control compositions. It is to be understood by those skilled in the art that such in vivo tests should be carried out under fasted conditions. In an in vivo crossover study a "test composition" of adsorbate and lipophilic microphase-forming material is dosed to half a group of test subjects and, after an appropriate washout period (e.g., one week) the same subjects are dosed with a control composition. As described above, the control composition may be either the first control composition, which consists of the adsorbate with no lipophilic microphase-forming material present, or the second control composition, which consists of an equivalent amount of the drug in crystalline form and an equivalent amount of the lipophilic microphase-forming material. The other half of the group is dosed with the control composition first, followed by the test composition. The relative bioavailability is measured as the concentration in the blood (serum or plasma) versus time area under the curve (AUC) determined for the test group divided by the AUC in the blood provided by the control composition. Preferably, this test/control ratio is determined for each subject, and then the ratios are averaged over all subjects in the study. In vivo determinations of AUC can be made by plotting the serum or plasma concentration of drug along the ordinate (y-axis) against time along the abscissa x-axis).

To demonstrate improved bioavailability relative to the first control composition and the second control composition, a "three-way in vivo crossover" study may be conducted where the three compositions are the test composition, the first control composition and the second composition.

A preferred embodiment is one in which the relative bioavailability of the test composition is at least 1.25 relative to either the first control composition or the second control composition when tested under fasted conditions. (That is, the AUC in the blood provided by the test composition is at least 1.25-fold the AUC provided by the control composition.) The relative bioavailability may be at least 2.0, and more preferably at least 3.0, relative to either control composition. The determination of AUCs is a well-known procedure and is described, for example, in Welling, "Pharmacokinetics Processes and Mathematics," ACS Monograph 185 (1986). An even more preferred embodiment of the present invention is one for which the relative bioavailability of the test composition is at least 1.25-fold relative to both the first control composition and the second control composition.

Alternatively, in another separate aspect, the compositions comprising an adsorbate and lipophilic microphase-forming material provide more regular absorption. In this aspect, the compositions provide a fed/fasted bioavailability ratio that is near 1.0. By "fed/fasted bioavailability ratio" is meant the AUC in the blood provided by a composition dosed to a subject in the fed state, divided by the AUC in the blood provided by the same composition dosed to a subject in the fasted state. By "subject in the fed state" is meant a subject who has eaten a Food and Drug Administration (FDA)-recommended standard high fat breakfast within a period of twenty minutes, and then ingested (i.e., swallowed) the test dosage form essentially immediately thereafter. A standard high-fat breakfast consists of, for example, two eggs fried in one tablespoon of butter, two strips of bacon, six ounces of hash brown potatoes, two pieces of toast with two teaspoons of butter and two pats of jelly, and eight ounces of whole milk. This standard high-fat breakfast contains approximately 964 calories, 54% supplied as fat (58 gm) and 12% supplied as protein, calculated using the monograph "Nutritive Value of Foods", U.S. Department of Agriculture Home and Garden Bulletin Number 72. Additional food can also be consumed within the twenty-minute period and the subject still qualifies as "fed". A "subject in the fasted state" for purposes of definition is one who has not eaten for at least eight hours, typically overnight, prior to ingestion of the dosage form.

Thus, a preferred composition of the present invention comprising an adsorbate and a lipophilic microphase forming material provides a fed/fasted bioavailability ratio of from about 0.5 to about 2.0. Preferably, the compositions provide a fed/fasted bioavailability ratio of from about 0.67 to about 1.5, and more preferably of from about 0.8 to about 1.25. Preferably, the composition of the present invention provides a fed/fasted bioavailability ratio that is closer to 1 than at least one of the first control compositions and the second composition, more preferably both compositions.

Alternatively, the concentration-enhancement provided by the compositions of the present invention may be determined in in vitro dissolution tests in an appropriate use environment. It has been determined that enhanced drug concentration in in vitro dissolution tests in a buffer solution is a good indicator of in vivo performance and bioavailability. One appropriate buffer solution is a PBS solution, which consists of 20 mM sodium phosphate ($Na_2HPO_4$), 47 mM potassium phosphate ($KH_2PO_4$), 87 mM NaCl, and 0.2 mM KCl, adjusted to pH 6.5 with NaOH. Another appropriate buffer solution is a MOPS solution, which consists of 50 mM 4-morpholinepropanesulfonic acid (MOPS) with 150 mM NaCl, adjusted to pH 7.4 with NaOH. In particular, a composition of the present invention may be dissolution-tested by adding it to either a PBS solution or a MOPS solution and agitating to promote dissolution. A composition of the invention is one that meets the criteria set out below when dosed to either solution.

Alternatively, the compositions comprising an adsorbate and a lipophilic microphase forming material provide concentration enhancement by reducing the mass of precipitate formed in the use environment relative to the control composition. Reducing the mass of precipitate results in an increase in the amount of drug present in drug forms that are more labile and mobile, resulting in an increase in relative bioavailability. As used herein, the "precipitate ratio" is defined as the mass of drug present in the precipitate obtained when a first control composition (e.g., the adsorbate alone) is administered to an aqueous use environment divided by the mass of drug present in the precipitate obtained when a test composition comprising the adsorbate and lipophilic microphase-forming material is administered to an equivalent amount of the same use environment. Thus, if 30 mg of drug is present in the precipitate formed when a control composition is administered to a test medium and 20 mg of drug is present in the precipitate formed when a test composition is administered to the same test medium, the precipitate ratio is equal to 1.5 (30/20). The compositions comprising an adsorbate and a lipophilic microphase forming material, following introduction to an aqueous environment of use, provide a precipitate ratio that is at least 1.25 relative to the first control composition previously described. Preferably, the composition of the present invention provides a precipitate ratio that is at least 2-fold, more preferably at least 3-fold relative to the control composition.

The amount of drug present in precipitate may be determined by any analytical technique that can quantitatively make such a determination. In one method, the amount of drug present in precipitate is determined by subtracting the total dissolved drug concentration from the theoretical concentration of drug if all of the drug added to the test medium had dissolved. As used herein, the term "total dissolved drug" refers to the total amount of drug dissolved in the aqueous solution, and includes drug present in the form of free drug, micelles, and lipophilic microphases. Specifically, this means that total dissolved drug may be determined by separating out any undissolved drug by centrifugation or filtration and then measuring the amount of drug remaining in the supernatant or filtrate. Total dissolved drug is typically taken as that material that either passes a 0.45 μm syringe filter or, alternatively, the material that remains in the supernatant following centrifugation. Filtration can be conducted using a 13 mm, 0.45 μm polyvinylidine difluoride syringe filter sold by Scientific Resources under the trademark TITAN®. Centrifugation is typically carried out in a polypropylene microcentrifuge tube by centrifuging at 13,000 G for 60 seconds. Other similar filtration or centrifugation methods can be employed and useful results obtained. For example, using other types of microfilters may yield values somewhat higher or lower (≈10-40%) than that obtained with the filter specified above but will still allow identification of preferred compositions.

Alternatively, drug in precipitate may be determined by collecting the solids obtained upon centrifugation or filtration of the aqueous solution, dissolution of the solids in an appropriate solvent, such as methanol, dimethylsulfoxide, or dimethylacetamide, and then analyzing for the drug using any quantitative analytical technique such as HPLC or NMR.

In another alternative aspect, the composition comprising an adsorbate and a lipophilic microphase forming material may provide a maximum total dissolved drug concentration (MDC) that is at least 1.25-fold the MDC of either the first control composition or the second control composition. In other words, if the MDC provided by either control composition is 100 μg/mL, then a composition comprising an adsorbate and lipophilic microphase-forming material provides a MDC of at least 125 μg/mL. More preferably, the MDC of drug achieved with the compositions of the present invention are at least 2-fold, and even more preferably at least 3-fold, that of either control composition. To facilitate testing, the maximum drug concentration may be taken as the maximum concentration achieved within 90 to 180 minutes following administration of the drug. Preferred compositions meet these criteria for both the first control composition and the second control composition:

Alternatively, the compositions comprising an adsorbate and a lipophilic microphase-forming material may provide in an aqueous use environment a total dissolved drug concentration versus time Area Under The Curve (AUC), for any period of at least 90 minutes between the time of introduction into the use environment and about 270 minutes following introduction to the use environment that is at least 1.25-fold that of either the first control composition or the second control composition. More preferably, the AUC achieved with the compositions of the present invention are at least 2-fold and more preferably at least 3-fold that of either control composition. Preferred compositions meet these criteria for both the first control composition and the second control composition.

In a particularly preferred embodiment of the present invention, the inventors have found that certain compositions provide a surprisingly "synergistic enhancement" in the various concentration and bioavailability criteria described above. The "synergistic enhancement" is determined by comparing the performance of the test composition of adsorbate and lipophilic microphase-forming material to a "third control composition." The third control composition consists essentially of the undispersed drug alone in its thermodynamically lowest energy state, typically the most stable crystalline form or its amorphous form if a crystalline form is unknown. Preferred compositions of drug/substrate adsorbate and lipophilic microphase-forming material exhibit synergistic enhancement by performing better than would be expected by simply adding the enhancement provided by an adsorbate with the enhancement provided by the lipophilic microphase-forming material.

To determine synergy, it is necessary to determine the performance of the first control composition, the second control composition, and the third control composition either in in vivo or in in vitro dissolution tests. The relative enhancement of the first control composition (e.g., the adsorbate but with no lipophilic microphase-forming material) is determined with respect to the third control composition. For example, if the first control composition provides an $AUC_{90}$ (that is, the AUC obtained during the first 90 minutes following introduction of the composition to a use environment) of 20,000 min*μg/ml and the third control composition provides an $AUC_{90}$ of 1,000 min*μg/ml, the first control composition has a relative enhancement of 20-fold.

Likewise, the relative enhancement of the second control composition (e.g., the crystalline drug alone with lipophilic microphase-forming material) is determined with respect to the third control composition. For example, if the second control composition provides an $AUC_{90}$ of 40,000 min*μg/ml and the third control composition provides an $AUC_{90}$ of 1,000 min*μg/ml, the second control composition has a relative enhancement of 40-fold.

Compositions of the present invention provide synergistic enhancement when the relative enhancement provided by the test composition compared with the third control composition is greater than the sum of the relative enhancement provided by the first control composition and the relative enhancement provided by second control composition. Returning to the examples described above, if the first control composition provided a relative enhancement of 20-fold, and the second control composition provided a relative enhancement of 40-fold, the sum of their relative enhancements would be 60-fold. Thus, a test composition provides synergistic enhancement when it provides a relative enhancement of greater than 60-fold compared with the third control composition.

The synergistic enhancement may also be determined by comparing the relative bioavailability of the test composition, first control composition, and second control composition relative to the third control composition. Synergistic enhancement would be shown where the relative bioavailability of the test composition is greater than the sum of the relative bioavailability of the first control composition and the relative bioavailability of the second control composition. For example, if the first control composition provides a relative bioavailability of 1.5 with respect to the third control composition, and the second control composition provides a relative bioavailability of 2.0 with respect to the third control composition, the test composition shows synergistic enhancement when it has a relative bioavailability relative to the third control composition greater than 3.5.

Excipients and Dosage Forms

Although the key ingredients present in the compositions are simply (1) the drug/substrate adsorbate, (2) the lipophilic microphase-forming material, and (3) the optional concentration-enhancing polymer, the inclusion of other excipients in the composition may be useful. These excipients may be utilized in order to formulate the composition into tablets, capsules, suppositories, suspensions, powders for suspension, creams, transdermal patches, depots, and the like.

Conventional matrix materials, complexing agents, fillers, disintegrating agents (disintegrants), or binders may be added as part of the composition itself or added by granulation via wet or mechanical or other means. These materials may comprise up to 90 wt % of the composition.

Examples of matrix materials, fillers, or diluents include lactose, mannitol, xylitol, microcrystalline cellulose, dibasic calcium phosphate (dihydrate and anhydrous), and starch.

Examples of disintegrants include sodium starch glycolate, sodium alginate, carboxy methyl cellulose sodium, methyl cellulose, and croscarmellose sodium, and crosslinked forms of polyvinyl pyrrolidone such as those sold under the trade name CROSPOVIDONE (available from BASF Corporation).

Examples of binders include methyl cellulose, microcrystalline cellulose, starch, and gums such as guar gum, and tragacanth.

Examples of lubricants include magnesium stearate, calcium stearate, and stearic acid.

Examples of preservatives include sulfites (an antioxidant), benzalkonium chloride, methyl paraben, propyl paraben, benzyl alcohol and sodium benzoate.

Examples of suspending agents or thickeners include xanthan gum, starch, guar gum, sodium alginate, carboxymethyl cellulose, sodium carboxymethyl cellulose, methyl cellulose, hydroxypropyl methyl cellulose, polyacrylic acid, silica gel, aluminum silicate, magnesium silicate, and titanium dioxide.

Examples of anticaking agents or fillers include silicon oxide and lactose.

Other conventional excipients may be employed in the compositions of this invention, including those excipients well-known in the art. Generally, excipients such as pigments, lubricants, flavorants, and so forth may be used for customary purposes and in typical amounts without adversely affecting the properties of the compositions. These excipients may be utilized in order to formulate the composition into tablets, capsules, suspensions, powders for suspension, creams, transdermal patches, and the like.

In particular, solid dosage forms such as immediate release tablets, controlled release tablets, delayed release tablets, chewable tablets and analogous capsules containing solid material are a preferred embodiment of this invention. Preferred dosage forms of this type generally comprise from 10 wt % lipophilic microphase-forming material up to 80 wt % lipophilic microphase-forming material as well as the drug/substrate adsorbate, together with other optional excipients.

It is conventionally thought that because lipophilic microphase-forming material are typically either low melting point or low $T_g$ solids, or even liquids at room temperature, that they are not considered appropriate additives for such solid dosage forms except at low levels, typically less than about 5 wt % or less to promote wetting and dissolution of the tablet. However, the inventors have found that, contrary to such conventional wisdom, solid dosage forms with excellent properties can be made that have relatively high levels of lipophilic microphase-forming material. In order for such high lipophilic microphase-forming material levels to be utilized in such solid dosage forms, the inventors have found it desirable to adsorb at least a portion of the lipophilic microphase-forming material on a solid substrate or disperse the lipophilic microphase-forming material in a water soluble or water dispersible matrix. As mentioned earlier, appropriate adsorption substrates include materials such as silicon oxide, dibasic calcium phosphate, microcrystalline cellulose, and calcium silicate. Appropriate water soluble or water dispersible dispersion matrix materials include sugars such as sucrose and xylitol, organic acids such as citric acid or lactic acid, water soluble polymers such as polydextrose, polyethylene oxide, or dextrin. Particularly preferred dispersion matrix materials are the concentration-enhancing polymers previously described. In a particularly preferred embodiment, the lipophilic microphase-forming material is co-adsorbed along with drug on a high surface area substrate. An added advantage of this embodiment, particularly when the lipophilic microphase-forming material is liquid at temperatures below about 50° C., is that relatively high levels of lipophilic microphase-forming material, up to about 50 wt % or in some cases even more, can often be used while still having the resulting material be a solid powder or granule at ambient conditions.

Compositions of this invention may also be used in a wide variety of dosage forms for administration of drugs. Exemplary dosage forms are powders or granules that may be taken orally either dry or reconstituted by addition of water or other liquids to form a paste, slurry, suspension or solution; tablets; capsules; multiparticulates; and pills. Various additives may be mixed, ground, or granulated with the compositions of this invention to form a material suitable for the above dosage forms. In one preferred embodiment, the drug/substrate adsorbate is dispersed in a vehicle that contains the lipophilic microphase-forming material.

The compositions of the present invention may be formulated in various forms such that they are delivered as a suspension of particles in a liquid vehicle. Such suspensions may be formulated as a liquid or paste at the time of manufacture, or they may be formulated as a dry powder with a liquid, typically water, added at a later time but prior to oral administration. Such powders that are constituted into a suspension are often termed sachets or oral powder for constitution (OPC) formulations. Such dosage forms can be formulated and reconstituted via any known procedure. The simplest approach is to formulate the dosage form as a dry powder that is reconstituted by simply adding water and agitating. Alternatively, the dosage form may be formulated as a liquid and a dry powder that are combined and agitated to form the oral suspension. In yet another embodiment, the dosage form can be formulated as two powders that are reconstituted by first adding water to one powder to form a solution to which the second powder is combined with agitation to form the suspension.

Generally, it is preferred that the composition be formulated for long-term storage in the dry state as this promotes the chemical and physical stability of the drug. Thus, a preferred embodiment is a solid dosage form comprising the adsorbate and lipophilic microphase-forming material.

Yet another method to deliver the adsorbate and lipophilic microphase-forming material is to co-administer the adsorbate and lipophilic microphase-forming material to an in vivo use environment. The adsorbate and lipophilic microphase-forming material may each be added separately to the in vivo use environment. Thus, when dosed orally, the adsorbate may be taken orally prior to the lipophilic microphase-forming material, at the same time, or after the lipophilic microphase-forming material has been taken orally. In general, if administered separately to an in vivo use environment, the adsorbate and the lipophilic microphase-forming material should be administered within about 60 minutes of each other, preferably within about 30 minutes of each other, more preferably within about 15 minutes of each other.

Since the present invention has an aspect that relates to the treatment of a condition or disorder by treatment with a combination of a drug/substrate adsorbate and a lipophilic microphase-forming material that may be co-administered separately, the invention also relates to combining separate pharmaceutical compositions in kit form. The kit comprises two separate pharmaceutical compositions: (1) a composition comprising the drug/substrate adsorbate; and (2) a composition comprising a lipophilic microphase-forming material. The amounts of (1) and (2) are such that, when co-administered separately, the condition or disorder is treated and/or remediated. The kit comprises a container for containing the separate compositions such as a divided bottle or a divided foil packet, wherein each compartment contains a plurality of dosage forms (e.g., tablets) comprising (1) or (2). Alternatively, rather than separating the active ingredient-containing dosage forms, the kit may contain separate compartments each of which contains a whole dosage which in turn comprises separate dosage forms. An example of this type of kit is a blister pack wherein each individual blister contains two (or more) tablets, one (or more) tablet(s) comprising pharmaceutical composition (1), and the second (or more) tablet(s) comprising pharmaceutical composition (2). Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician. In the case of the instant invention a kit therefore comprises (1) a therapeutically effective amount of a composition comprising a solid adsorbate of a low-solubility drug and high surface area substrate, in a first dosage form;
(2) a therapeutically effective amount of a composition comprising a lipophilic microphase-forming material, in a second dosage form; and
(3) a container for containing said first and second dosage forms.

An example of such a kit, alluded to above, is a so-called blister pack. Blister packs are well known in the packaging industry and are widely used for the packaging of pharmaceutical unit dosage forms such as tablets, capsules, and the like. Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. Tablet(s) or capsule(s) can then be removed via said opening.

It may be desirable to provide a memory aid on the kit, e.g., in the form of numbers next to the tablets or capsules whereby the numbers correspond with the days of the regimen during which the tablets or capsules so specified should be ingested. Another example of such a memory aid is a calendar printed on the card, e.g., as follows "First Week, Monday, Tuesday, . . . etc. . . . Second Week, Monday, Tuesday, . . . ", etc. Other variations of memory aids will be readily apparent. A "daily dose" can be a single tablet or capsule or several pills or capsules to be taken on a given day. Also a daily dose of the first compound can consist of one tablet or capsule while a daily dose of the second compound can consist of several tablets or capsules and vice versa. The memory aid should reflect this.

Compositions of the present invention may be used to treat any condition that is subject to treatment by administering a drug.

Other features and embodiments of the invention will become apparent from the following examples that are given for illustration of the invention rather than for limiting its intended scope.

EXAMPLES

Adsorbate 1

The following process was used to form a drug/substrate adsorbate containing 50 wt % [2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, "Drug 1", and 50 wt % CAB-O-SIL M-5P (fumed silica from Cabot Corporation, Midland, Mich.) as a substrate (surface area of about 200 m²/gm). First, a spray solution was formed containing 10 g Drug 1, 10 g CAB-O-SIL, and 380 g acetone as follows. CAB-O-SIL was added to acetone and the mixture was sonicated using a Fisher Scientific SF15 sonicator for 30 minutes to ensure full suspension and homogeneity. Drug 1 was then dissolved in this suspension by stirring for 15 minutes. The spray solution was pumped using a Bran+ Luebbe small volume high-pressure pump, to a spray drier (a Niro type XP Portable Spray-Dryer with a Liquid-Feed Process Vessel ("PSD-1")), equipped with a pressure nozzle (Spraying Systems Pressure Nozzle and Body) (SK 80-16). The PSD-1 was equipped with a 9-inch chamber extension. The 9-inch chamber extension was added to the spray dryer to increase the vertical length of the dryer. The added length increased the residence time within the dryer, which allowed the product to dry before reaching the angled section of the spray dryer. The spray drier was also equipped with a 316 SS circular diffuser plate with 1/16-inch drilled holes, having a 1% open area. This small open area directed the flow of the drying gas to minimize product recirculation within the spray dryer. The nozzle sat flush with the diffuser plate during operation. The high-pressure pump was followed by a pulsation dampener to minimize pulsation at the nozzle. The spray solution was pumped to the spray drier at a pressure of 350 psig. Drying gas (nitrogen) was circulated through the diffuser plate at an inlet temperature of 100° C. The evaporated solvent and wet drying gas exited the spray drier at a temperature of 34.5° C. The drug/substrate adsorbate formed by this process was collected in a cyclone, and was post-dried using a Gruenberg single-pass convection tray dryer operating at 30° C. for 16 hours.

Example 1

In Vitro Dissolution Test

This test demonstrates the present invention in vitro. Example 1 consisted of Adsorbate 1 administered in solution with a lipophilic microphase-forming material. At time 0, a 4 mg sample of Adsorbate 1 was added to 40 mL phosphate buffered saline (PBS) at pH 6.5 and 290 mOsm/kg, containing 1 mg/mL of the lipophilic microphase-forming material Cremaphor RH40 (available from BASF of Mount Olive, N.J.). The concentration of drug would have been 50 µg/mL, if all of the drug had dissolved. The test solution was stirred at room temperature in a syringe equipped with a Gelman Acrodisc 13 CR 0.45 µm PTFE filter. At each sample time, 1 to 2 mL test solution was pushed through the filter and analyzed using UV to determine the concentration of Drug 1 in solution. Samples were collected at 0.5, 1, 2, 3, 5, 10, 15, 20, 30, 45, 60, 90, 120, 150, 250 and 1200 minutes. The results are shown in Table 1.

Control 1

Control 1 consisted of Adsorbate 1 administered into PBS without the lipophilic microphase-forming material, and a sufficient amount of adsorbate was added so that the concentration of drug would have been 50 µg/mL, if all of the drug had dissolved. An in vitro dissolution test was performed with Control 1 using the procedures outlined for Example 1 and the results are shown in Table 1.

Control 2

Control 2 consisted of crystalline Drug 1 administered into PBS containing 1 mg/mL of the lipophilic microphase-forming material Cremaphor RH40, and a sufficient amount of Drug 1 was added so that the concentration would have been 50 µg/mL, if all of the drug had dissolved. An in vitro dissolution test was performed with Control 2 using the procedures outlined for Example 1 and the results are shown in Table 1.

Control 3

Control 3 consisted of crystalline Drug 1 administered into PBS without the lipophilic microphase-forming material, and a sufficient amount of crystalline Drug 1 was added so that the concentration of drug would have been 50 µg/mL, if all of the drug had dissolved. An in vitro dissolution test was performed with Control 3 using the procedures outlined for Example 1 and the results are shown in Table 1.

TABLE 1

| Example | Time (min) | Drug 1 Concentration (µg/mL) | AUC (min * µg/mL) |
|---|---|---|---|
| 1 | 0 | <0.5 | 0 |
| | 0.5 | <0.5 | 0 |
| | 1 | <0.5 | <1 |
| | 2 | <0.5 | <1 |
| | 3 | 0.6 | 2 |
| | 5 | 1.2 | 3 |
| | 10 | 2.9 | 14 |
| | 15 | 3.5 | 30 |
| | 20 | 4.8 | 50 |
| | 30 | 6.9 | 109 |
| | 45 | 9.8 | 234 |
| | 60 | 12.3 | 400 |
| | 90 | 17.0 | 840 |
| | 120 | 18.3 | 1370 |
| | 150 | 20.9 | 1960 |
| | 250 | 22.2 | 4120 |
| | 1200 | 10.5 | 18,500 |
| Control 1 | 0 | <0.5 | 0 |
| | 0.5 | <0.5 | 0 |
| | 1 | <0.5 | <1 |
| | 2 | <0.5 | <1 |
| | 3 | <0.5 | <2 |
| | 5 | <0.5 | <3 |
| | 10 | <0.5 | <5 |
| | 15 | <0.5 | <8 |
| | 20 | <0.5 | <10 |
| | 30 | <0.5 | <15 |
| | 45 | <0.5 | <23 |
| | 60 | <0.5 | <30 |
| | 90 | <0.5 | <45 |
| | 120 | <0.5 | <60 |
| | 150 | <0.5 | <75 |
| Control 2 | 0 | <0.5 | 0 |
| | 0.5 | <0.5 | 0 |
| | 1 | <0.5 | <1 |
| | 2 | <0.5 | <1 |
| | 3 | <0.5 | <2 |
| | 5 | <0.5 | <3 |
| | 10 | <0.5 | <5 |
| | 15 | <0.5 | <8 |
| | 20 | <0.5 | <10 |
| | 30 | <0.5 | <15 |
| | 45 | <0.5 | <23 |
| | 60 | 0.7 | 31 |
| | 90 | 1.0 | 56 |
| | 120 | 1.1 | 88 |
| | 250 | 2.2 | 307 |
| | 1200 | 4.3 | 3400 |
| Control 3 | 0 | <0.5 | 0 |
| | 1 | <0.5 | <1 |
| | 3 | <0.5 | <2 |
| | 5 | <0.5 | <3 |
| | 10 | <0.5 | <5 |
| | 15 | <0.5 | <8 |
| | 20 | <0.5 | <10 |
| | 30 | <0.5 | <15 |
| | 45 | <0.5 | <23 |
| | 60 | <0.5 | <30 |
| | 90 | <0.5 | <45 |
| | 120 | <0.5 | <60 |
| | 1200 | <0.5 | <600 |

The results of these tests are summarized in Table 2, which shows the maximum concentration of Drug 1 in solution during the first 90 minutes of the test ($MDC_{90}$), and the area under the aqueous concentration versus time curve after 90 minutes ($AUC_{90}$).

TABLE 2

| Example | $MDC_{90}$ (µg/mL) | $AUC_{90}$ (min * µg/mL) |
|---|---|---|
| 1 | 17.0 | 840 |
| Control 1 | <0.5 | <45 |
| Control 2 | 1.0 | 56 |
| Control 3 | <0.5 | <45 |

These results show that the compositions of the present invention provided enhancement over the compositions of Controls 1, 2, and 3. Example 1 provided a $MDC_{90}$ that was at least greater than 34.0-fold that of Control 1, 17.0-fold that of Control 2, and at least greater than 34.0-fold that of Control 3. Example 1 also provided an $AUC_{90}$ that was at least greater than 18.7-fold that of Control 1, 15.0-fold that of Control 2, and at least greater than 18.7-fold that of Control 3.

Example 2

In Vitro Dissolution Test

Example 2 consisted of Adsorbate 1 administered in solution with a different lipophilic microphase-forming material. At time 0, a 4 mg sample of Adsorbate 1 was added to 40 mL phosphate buffered saline (PBS) at pH 6.5 and 290 mOsm/kg, containing 1 mg/mL of 5/2 (wt/wt) Cremaphor RH40/Capmul MCM (available from Abitec of Janesville, Wis.); the concentration of drug would have been 50 µg/mL, if all of the drug had dissolved. The test solution was stirred at room temperature in a syringe equipped with a Gelman Acrodisc 13 CR 0.45 µm PTFE filter, as described for Example 1. Samples were collected and analyzed using UV to determine the concentration of Drug 1 in solution. The results are shown in Table 3.

Control 4

Control 4 consisted of crystalline Drug 1 administered into PBS containing 5/2 (wt/wt) Cremophor RH40/Capmul MCM, and a sufficient amount of Drug 1 was added so that the concentration would have been 50 µg/mL, if all of the drug had dissolved. The results are shown in Table 3.

TABLE 3

| Example | Time (min) | Drug 1 Concentration (µg/mL) | AUC (min * µg/mL) |
|---|---|---|---|
| 2 | 0 | <0.5 | 0 |
| | 0.5 | <0.5 | 0 |
| | 1 | <0.5 | <1 |
| | 2 | <0.5 | <1 |
| | 3 | <0.5 | <2 |
| | 5 | 0.8 | 3 |
| | 10 | 2.2 | 10 |
| | 15 | 4.1 | 26 |
| | 20 | 4.7 | 48 |
| | 30 | 6.3 | 103 |
| | 45 | 8.8 | 216 |
| | 60 | 11.1 | 364 |
| | 90 | 15.3 | 761 |
| | 120 | 17.7 | 1260 |
| | 150 | 19.1 | 1810 |
| | 300 | 19.9 | 4650 |
| | 1380 | 10.1 | 20,900 |
| Control 4 | 0 | <0.5 | 0 |
| | 0.5 | <0.5 | 0 |
| | 1 | <0.5 | <1 |
| | 2 | <0.5 | <1 |

TABLE 3-continued

| Example | Time (min) | Drug 1 Concentration (µg/mL) | AUC (min * µg/mL) |
|---|---|---|---|
| | 3 | <0.5 | <2 |
| | 5 | <0.5 | <3 |
| | 10 | <0.5 | <5 |
| | 15 | <0.5 | <8 |
| | 20 | <0.5 | <10 |
| | 30 | 0.8 | 17 |
| | 45 | 0.7 | 28 |
| | 60 | 1.0 | 40 |
| | 90 | 0.9 | 68 |
| | 120 | 1.2 | 99 |
| | 150 | 1.5 | 140 |
| | 300 | 1.5 | 340 |
| | 1380 | 5.4 | 4050 |

The results of these tests are summarized in Table 4, which shows the maximum concentration of Drug 1 in solution during the first 90 minutes of the test ($MDC_{90}$), and the area under the aqueous concentration versus time curve after 90 minutes ($AUC_{90}$). Controls 1 and 3 are shown again for comparison.

TABLE 4

| Example | $MDC_{90}$ (µg/mL) | $AUC_{90}$ (min * µg/mL) |
|---|---|---|
| 2 | 15.3 | 761 |
| Control 4 | 0.9 | 68 |
| Control 1 | <0.5 | <45 |
| Control 3 | <0.5 | <45 |

These results show that the concentrations provided by the present invention were much greater than the concentrations provided by the controls. Example 2 provided a $MDC_{90}$ that was 17.0-fold that of Control 4, at least greater than 30.6-fold that of Control 1, and at least greater than 30.6-fold that of Control 3. Example 2 also provided an $AUC_{90}$ that was 11.2-fold that of Control 4, at least greater than 16.9-fold that of Control 1, and at least greater than 16.9-fold that of Control 3.

Adsorbate 2

The following process was used to form a drug/substrate adsorbate containing 30 wt % [2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester, "Drug 2", and 70 wt % CAB-O-SIL M-5P as a substrate. First, a spray solution was formed containing 122.0 mg Drug 2, 200.7 mg CAB-O-SIL M-5P, and 20 g acetone as follows. CAB-O-SIL was added to acetone and the mixture was sonicated using a Fisher Scientific SF15 sonicator for 30 minutes to ensure full suspension and homogeneity. Drug 2 was then dissolved in this suspension by stirring for 15 minutes. This suspension was then pumped into a "mini" spray-drying apparatus via a Cole Parmer 74900 series rate-controlling syringe pump at a rate of 1.0 mL/min. The spray-drying apparatus used a Spraying Systems Co. two-fluid nozzle, model number SU1A, with nitrogen as the atomizing gas. The nitrogen was pressurized and heated to a temperature of 55° C. and had a flow rate of about 1 standard $ft^3$/min (SCFM). The suspension was sprayed from the top of an 11-cm diameter stainless steel chamber. The resulting drug/substrate adsorbate was collected on Whatman 1 filter paper, dried under vacuum, and stored in a desiccator.

Example 3

In Vitro Dissolution Test

Example 3 consisted of Adsorbate 2 administered into solution with a lipophilic microphase-forming material. At time 0, a 6.656 mg sample of Adsorbate 2 was added to 40 mL of phosphate buffered saline (PBS) at pH 6.5 and 290 mOsm/kg, containing 1 mg/mL of PEG 6000 distearate (the concentration of drug would have been 50 µg/mL, if all of the drug had dissolved). The test solution was stirred at room temperature in a syringe equipped with a Gelman Acrodisc 13 CR 0.45 µm PTFE filter, as described for Example 1. Samples were collected and analyzed using UV to determine the concentration of Drug 2 in solution. The results are shown in Table 5.

Control 5

Control 5 consisted of Adsorbate 2 administered into PBS without the lipophilic microphase-forming material, and a sufficient amount of sample was added so that the concentration of drug would have been 50 µg/mL, if all of the drug had dissolved.

Control 6

Control 6 consisted of crystalline Drug 2 administered into PBS containing PEG 6000 Distearate, and a sufficient amount of Drug 2 was added so that the concentration would have been 50 µg/mL, if all of the drug had dissolved.

Control 7

Control 7 consisted of crystalline Drug 2 administered into PBS without the lipophilic microphase-forming material, and a sufficient amount of sample was added so that the concentration of drug would have been 50 µg/mL, if all of the drug had dissolved.

TABLE 5

| Example | Time (min) | Drug 2 Concentration (µg/mL) | AUC (min * µg/mL) |
|---|---|---|---|
| 3 | 0 | <0.5 | 0 |
| | 0.5 | <0.5 | 0 |
| | 1 | 0.7 | 1 |
| | 2 | 1.2 | 1 |
| | 3 | 1.6 | 3 |
| | 5 | 1.8 | 6 |
| | 10 | 2.0 | 16 |
| | 15 | 2.5 | 27 |
| | 20 | 2.4 | 39 |
| | 30 | 2.7 | 65 |
| | 45 | 2.7 | 105 |
| | 60 | 3.0 | 147 |
| | 90 | 3.2 | 239 |
| Control 5 | 0 | <0.5 | 0 |
| | 60 | <0.5 | <30 |
| | 120 | <0.5 | <60 |
| | 210 | <0.5 | <105 |
| | 1200 | 1.0 | 823 |
| Control 6 | 0 | <0.5 | 0 |
| | 0.5 | <0.5 | 0 |
| | 1 | <0.5 | <1 |
| | 2 | <0.5 | <1 |
| | 3 | <0.5 | <2 |
| | 5 | <0.5 | <3 |
| | 10 | <0.5 | <5 |
| | 15 | <0.5 | <8 |

TABLE 5-continued

| Example | Time (min) | Drug 2 Concentration (μg/mL) | AUC (min * μg/mL) |
|---|---|---|---|
| | 20 | <0.5 | <10 |
| | 30 | <0.5 | <15 |
| | 45 | <0.5 | <23 |
| | 60 | <0.5 | <30 |
| | 90 | <0.5 | <45 |
| Control 7 | 0 | <0.5 | 0 |
| | 1 | <0.5 | <1 |
| | 2 | <0.5 | <1 |
| | 3 | <0.5 | <2 |
| | 5 | <0.5 | <3 |
| | 10 | <0.5 | <5 |
| | 15 | <0.5 | <8 |
| | 20 | <0.5 | <10 |
| | 30 | <0.5 | <15 |
| | 45 | <0.5 | <23 |
| | 64 | <0.5 | <32 |
| | 90 | <0.5 | <45 |
| | 160 | <0.5 | <80 |
| | 1200 | <0.5 | <600 |

The results of these tests are summarized in Table 6, which shows the maximum concentration of Drug 2 in solution during the first 90 minutes of the test ($MDC_{90}$), and the area under the aqueous concentration versus time curve after 90 minutes ($AUC_{90}$).

TABLE 6

| Example | $MDC_{90}$ (μg/mL) | $AUC_{90}$ (min * μg/mL) |
|---|---|---|
| 3 | 3.2 | 239 |
| Control 5 | <0.5 | <45 |
| Control 6 | <0.5 | <45 |
| Control 7 | <0.5 | <45 |

These results show that the concentrations provided by the present invention were much greater than the concentrations provided by the controls. Example 3 provided a $MDC_{90}$ that was at least greater than 6.4-fold that of Control 5, at least greater than 6.4-fold that of Control 6, and at least greater than 6.4-fold that of Control 7. Example 3 also provided an $AUC_{90}$ that was at least greater than 5.3-fold that of Control 5, at least greater than 5.3-fold that of Control 6, and at least greater than 5.3-fold that of Control 7.

Adsorbate 3

The following process was used to form a drug/substrate adsorbate containing 25 wt % 5-(2-(4-(3-benzisothiazolyl)-piperazinyl)ethyl-6-chlorooxindole, "Drug 3", and 75 wt % CAB-O-SIL M-5P as a substrate. A spray solution was formed containing 62.5 mg Drug 3, 187.5 mg CAB-O-SIL M-5P, and 40 g acetone/water (9/1), and spray dried using the "mini" spray-drying apparatus described for Adsorbate 2. The suspension was pumped into the "mini" spray drier at a rate of 1.3 mL/min, and the nitrogen atomizing gas was heated to a temperature of 70° C.

Example 4

In Vitro Dissolution Test

Example 4 consisted of Adsorbate 3 administered into solution with a lipophilic microphase-forming material. At time 0, an 8.02 mg sample of Adsorbate 3 was added to 40 ml of 50 mM 3-(4-morpholino propane sulfonic acid) sodium salt (MOPS) buffer at pH 7.4, containing 5 mg/mL of Tween 80 (available from ICI Americas Inc); the concentration of drug would have been 50 μg/mL, if all of the drug had dissolved. The test solution was stirred at room temperature in a syringe equipped with a Gelman Acrodisc 13 CR 0.45 μm PTFE filter, as described for Example 1. Samples were collected and analyzed using UV to determine the concentration of Drug 3 in solution. The results are shown in Table 7.

Control 8

Control 8 consisted of Adsorbate 3 administered into PBS without the lipophilic microphase-forming material, and a sufficient amount of sample was added so that the concentration of drug would have been 50 μg/mL, if all of the drug had dissolved.

Control 9

Control 9 consisted of crystalline Drug 3 administered into PBS containing Tween 80, and a sufficient amount of Drug 3 was added so that the concentration would have been 50 μg/mL, if all of the drug had dissolved.

Control 10

Control 10 consisted of crystalline Drug 3 administered into PBS without the lipophilic microphase-forming material, and a sufficient amount of sample was added so that the concentration of drug would have been 50 μg/mL, if all of the drug had dissolved.

TABLE 7

| Example | Time (min) | Drug 3 Concentration (μg/mL) | AUC (min * μg/mL) |
|---|---|---|---|
| 4 | 0 | 0 | 0 |
| | 0.5 | 17 | 4 |
| | 1 | 15 | 12 |
| | 2 | 12 | 26 |
| | 3 | 11 | 37 |
| | 5 | 9 | 57 |
| | 10 | 9 | 101 |
| | 15 | 7 | 140 |
| | 20 | 6 | 173 |
| | 30 | 6 | 232 |
| | 45 | 5 | 315 |
| | 60 | 5 | 395 |
| | 90 | 5 | 545 |
| | 120 | 5 | 690 |
| | 1250 | 4 | 5640 |
| Control 8 | 0 | <1 | 0 |
| | 0.5 | <1 | <1 |
| | 1 | <1 | <1 |
| | 2 | <1 | <2 |
| | 3 | <1 | <3 |
| | 5 | <1 | <5 |
| | 15 | <1 | <15 |
| | 20 | <1 | <20 |
| | 30 | <1 | <30 |
| | 45 | <1 | <45 |
| | 60 | <1 | <60 |
| | 84 | <1 | <84 |
| | 150 | <1 | <150 |
| Control 9 | 0 | <1 | 0 |
| | 0.5 | <1 | <1 |
| | 1 | <1 | <1 |
| | 2 | <1 | <2 |
| | 3 | <1 | <3 |
| | 5 | <1 | <5 |
| | 10 | <1 | <10 |

TABLE 7-continued

| Example | Time (min) | Drug 3 Concentration (μg/mL) | AUC (min * μg/mL) |
|---|---|---|---|
| | 15 | <1 | <15 |
| | 20 | <1 | <20 |
| | 30 | <1 | <30 |
| | 45 | 1 | 45 |
| | 60 | 1 | 60 |
| | 90 | 2 | 120 |
| | 1245 | 2 | 2430 |
| Control 10 | 0 | <1 | <1 |
| | 5 | <1 | <5 |
| | 10 | <1 | <10 |
| | 20 | <1 | <20 |
| | 40 | <1 | <40 |
| | 90 | <1 | <90 |
| | 1260 | <1 | <1260 |

The results of these tests are summarized in Table 8, which shows the maximum concentration of Drug 3 in solution during the first 90 minutes of the test ($MDC_{90}$), and the area under the aqueous concentration versus time curve after 90 minutes ($AUC_{90}$).

TABLE 8

| Example | $MDC_{90}$ (μg/mL) | $AUC_{90}$ (min * μg/mL) |
|---|---|---|
| 4 | 17 | 545 |
| Control 8 | <1 | <90 |
| Control 9 | 2 | 120 |
| Control 10 | <1 | <90 |

These results show that the concentrations provided by the present invention were much greater than the concentrations provided by the controls. Example 4 provided a $MDC_{90}$ that was at least greater than 17.0-fold that of Control 8, 8.5-fold that of Control 9, and at least greater than 17.0-fold that of Control 10. Example 4 also provided an $AUC_{90}$ that was at least greater than 6.1-fold that of Control 8, 4.5-fold that of Control 9, and at least greater than 6.1-fold that of Control 10.

The terms and expressions which have been employed in the foregoing specification are used therein as terms of description and not of limitation, an there is no intention, in the use of such terms and expressions, of excluding equivalents of the features shown and described or portions thereof, it being recognized that the scope of the invention is defined and limited only by the claims which follow.

The invention claimed is:

1. A composition comprising:
(a) a spray-dried solid dispersion adsorbate comprising a completely amorphous drug and a concentration enhancing polymer adsorbed onto an inorganic oxide substrate, and wherein said drug in said adsorbate is substantially completely amorphous and
(b) a lipophilic microphase-forming material selected from the group consisting of medium-chain glyceryl mono-, di-, and tri-alkylates, sorbitan esters, fatty acid esters, polyoxyethylene sorbitan fatty acid esters, alpha tocopheryl polyethylene glycol 1000 succinate (TPGS), and mixtures thereof; said composition having a mass ratio of said lipophilic microphase-forming material to said drug of from 0.1 to 500, and wherein said lipophilic microphase forming material is co-adsorbed with said drug onto said substrate of the spray-dried solid dispersion adsorbate; wherein said lipophilic microphase-forming material is water immiscible and said drug has a partition coefficient $K_p$ between a use environment.

2. The composition of claim 1 wherein said lipophilic microphase-forming material is present in a sufficient amount so that said composition provides concentration enhancement of said drug in a use environment relative to at least one of a first control composition and a second control composition; wherein (i) said first control composition consists essentially of an equivalent amount of said solid adsorbate with no lipophilic microphase-forming material present; (ii) said second control composition consists essentially of an equivalent amount of said drug in unadsorbed form with an equivalent amount of said lipophilic, microphase-forming material.

3. The composition of claim 2 wherein said composition provides a relative bioavailability of at least 1.25-fold relative to at least one of said first control composition and said second control composition.

4. The composition of claim 1 wherein said lipophilic microphase-forming material forms lipophilic microphases in said use environment having a characteristic diameter of less than about 100 μm.

5. The composition of claim 1 wherein said mass ratio of said lipophilic microphase-forming material to said drug is from 0.1 to 100.

6. The composition of claim 1 wherein said solid adsorbate and said lipophilic microphase-forming material are both present in a single dosage form.

7. The composition of claim 1 wherein said composition is solid at 25° C.

8. The composition of claim 1 wherein said composition provides synergistic enhancement.

9. The composition of claim 1 wherein said drug is selected from the group consisting of antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, antidepressants, and antiviral agents, glycogen phosphorylase inhibitors, and cholesteryl ester transfer protein inhibitors.

10. The composition of claim 1 wherein said concentration-enhancing polymer is selected from the group consisting of hydroxypropyl methyl cellulose acetate succinate, hydroxypropyl methyl cellulose phthalate, cellulose acetate phthalate, cellulose acetate trimellitate, carboxymethyl ethyl cellulose, hydroxypropyl methyl cellulose, poloxamers, polyvinylpyrrolidone, polyvinyl alcohols that have at least a portion of their repeat units in hydrolyzed form, and mixtures thereof.

11. The composition of claim 1 further comprising a second concentration-enhancing polymer wherein said second concentration enhancing polymer is not adsorbed to said substrate.

12. The composition of claim 11 wherein said second concentration-enhancing polymer is selected from the group consisting of hydroxypropyl methyl cellulose acetate succinate, hydroxypropyl methyl cellulose phthalate, cellulose acetate phthalate, cellulose acetate trimellitate, carboxymethyl ethyl cellulose, hydroxypropyl methyl cellulose, poloxamers, polyvinylpyrrolidone, polyvinyl alcohols that have at least a portion of their repeat units in hydrolyzed form, and mixtures thereof.

13. A solid dosage form comprising the composition of claim 1, wherein said lipophilic, microphase-forming material comprises from 10wt % to 80wt % of said solid dosage form, and said dosage form is selected from the group consisting of a tablet and a capsule.

14. The composition of claim 1 wherein said substrate is selected from the group consisting of $SiO_2$, $TiO_2$, $ZnO_2$, $ZnO$, $Al_2O_3$, MgAlSilicate, CaSilicate, $AlOH_2$, zeolites, and inorganic molecular sieves.

15. The composition of claim 1 wherein said lipophilic microphase-forming material is selected from sorbitan fatty acid esters, alpha tocopheryl polyethylene glycol 1000succinate (TPGS), and mixtures thereof.

16. The composition of claim 1 wherein said solid adsorbate is formed by spraying a spray suspension comprising said drug, said lipophilic microphase-forming material, and said concentration-enhancing polymer, dissolved in a solvent having said substrate suspended therein, and the solvent is removed to form a solid powder in less than 100 seconds.

\* \* \* \* \*